US009486589B2

(12) United States Patent
Hunter et al.

(10) Patent No.: US 9,486,589 B2
(45) Date of Patent: Nov. 8, 2016

(54) AUTOMATED METHOD FOR SIMULTANEOUS BUBBLE DETECTION AND EXPULSION

(71) Applicant: Massachusetts Institute of Technology, Cambridge, MA (US)

(72) Inventors: Ian W. Hunter, Lincoln, MA (US); Ashin P. Modak, Cupertino, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/528,771

(22) Filed: Oct. 30, 2014

(65) Prior Publication Data
US 2015/0122338 A1 May 7, 2015

Related U.S. Application Data

(60) Provisional application No. 61/898,516, filed on Nov. 1, 2013.

(51) Int. Cl.
*A61M 5/36* (2006.01)
*A61M 5/31* (2006.01)
(Continued)

(52) U.S. Cl.
CPC ........... *A61M 5/36* (2013.01); *A61M 5/16859* (2013.01); *A61M 5/3146* (2013.01); *A61M 2005/1402* (2013.01); *A61M 2005/3123* (2013.01);
(Continued)

(58) Field of Classification Search
CPC .................... A61M 5/16831; A61M 5/16859; A61M 5/3146; A61M 5/36; A61M 5/365; A61M 2005/1402; A61M 2005/1403; A61M 2005/3123
See application file for complete search history.

(56) References Cited

U.S. PATENT DOCUMENTS 4,498,088 A 2/1985 Kanayama
5,059,171 A 10/1991 Bridge et al.
(Continued)

FOREIGN PATENT DOCUMENTS

WO WO 02/064195 A2 8/2002
WO WO 2008/042721 A2 4/2008
(Continued)

OTHER PUBLICATIONS

International Search Report and Written Opinion of the International Searching Authority for International Application No. PCT/US2014/063196, entitled "Automated Method for Simultaneous Bubble Detection and Expulsion", mailed Jan. 29, 2015, 10 pages.

*Primary Examiner* — Imani Hayman
*Assistant Examiner* — James D Ponton
(74) *Attorney, Agent, or Firm* — Hamilton, Brook, Smith & Reynolds, P.C.

(57) ABSTRACT

A method and apparatus for detecting and removing air from a syringe containing a volume of liquid and a volume of gas is described. The method includes moving a piston in the syringe to expel gas through an orifice of the syringe, sensing a movement of the piston in the syringe, and determining when the volume of gas is expelled from the syringe based on a change in the sensed movement. Moving the piston may include applying oscillating force to the piston using an electromagnetic actuator, and displacement and speed of the piston during each oscillation may be sensed. Determining when the volume of gas is expelled may be based on a change in the sensed movement of the piston during one or more oscillations of the piston or based on a comparison to a given reference value.

25 Claims, 22 Drawing Sheets

(51) Int. Cl.
*A61M 5/168* (2006.01)
*G01B 21/16* (2006.01)
*G01F 17/00* (2006.01)
*G01P 3/02* (2006.01)
*A61M 5/14* (2006.01)

(52) U.S. Cl.
CPC ......... *A61M2205/332* (2013.01); *G01B 21/16* (2013.01); *G01F 17/00* (2013.01); *G01P 3/02* (2013.01); *Y10T 137/0324* (2015.04); *Y10T 137/2931* (2015.04)

(56) References Cited

U.S. PATENT DOCUMENTS

| | | | |
|---|---|---|---|
| 5,205,819 A | 4/1993 | Ross et al. | |
| 5,500,657 A | 3/1996 | Yauchi et al. | |
| 5,823,747 A | 10/1998 | Ciavarini et al. | |
| 7,987,722 B2 | 8/2011 | Hills | |
| 2004/0024361 A1* | 2/2004 | Fago | A61M 5/31525 604/152 |
| 2006/0206057 A1* | 9/2006 | DeRuntz | A61M 5/31551 604/224 |
| 2007/0062251 A1* | 3/2007 | Anex | A61M 5/14244 73/1.36 |
| 2009/0112155 A1* | 4/2009 | Zhao | A61M 5/14212 604/67 |
| 2010/0262078 A1* | 10/2010 | Blomquist | A61M 5/14244 604/151 |
| 2011/0009821 A1* | 1/2011 | Jespersen | A61M 5/1452 604/135 |
| 2011/0082388 A1* | 4/2011 | Hunter | A61B 10/0045 600/573 |
| 2011/0152757 A1* | 6/2011 | Beck | A61M 5/1452 604/67 |
| 2011/0270188 A1* | 11/2011 | Caffey | A61M 5/14526 604/151 |
| 2011/0282273 A1* | 11/2011 | Evans | A61M 13/003 604/24 |

FOREIGN PATENT DOCUMENTS

| | | |
|---|---|---|
| WO | WO 2011/097487 A2 | 8/2011 |
| WO | WO 2015/066346 A1 | 5/2015 |

* cited by examiner

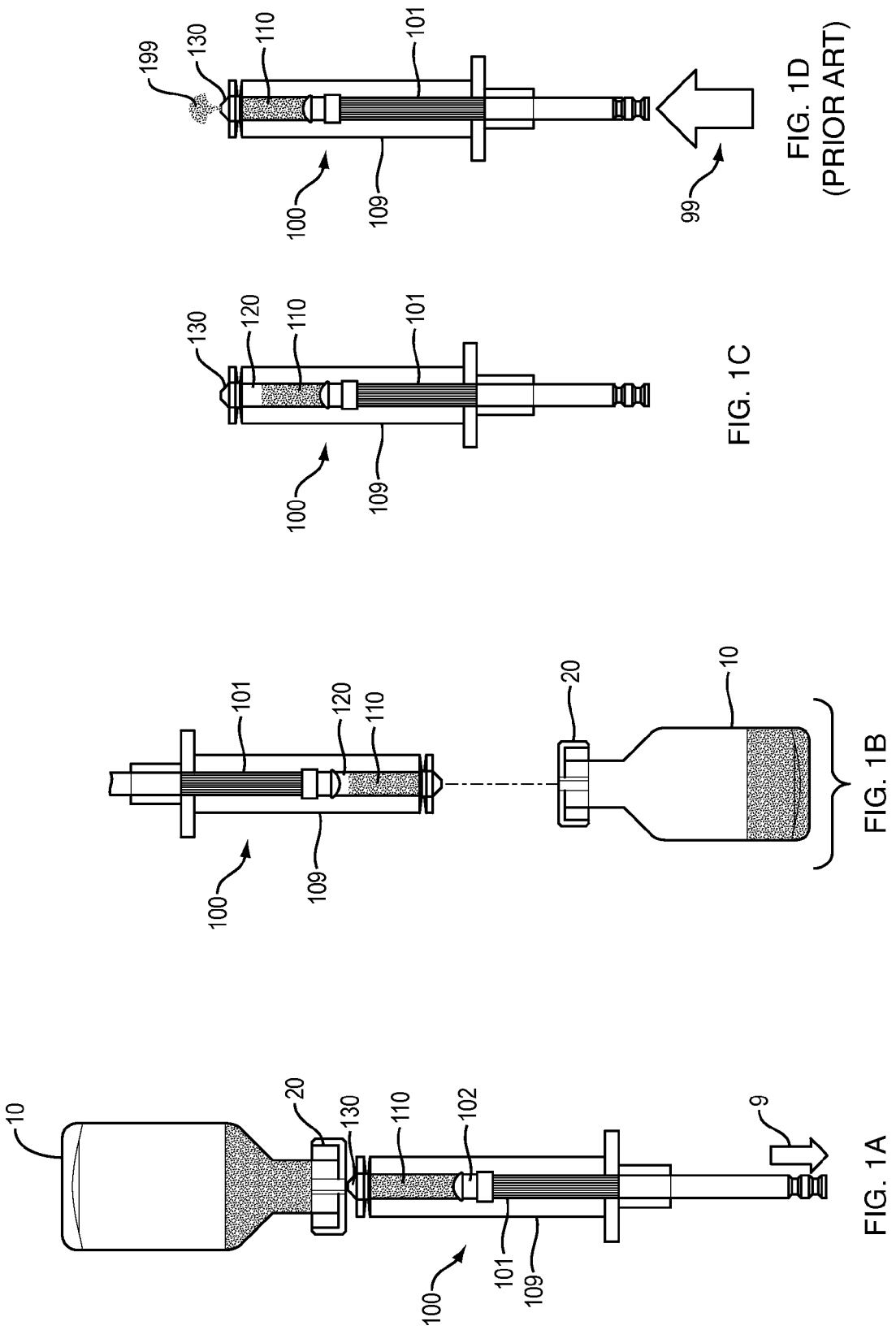

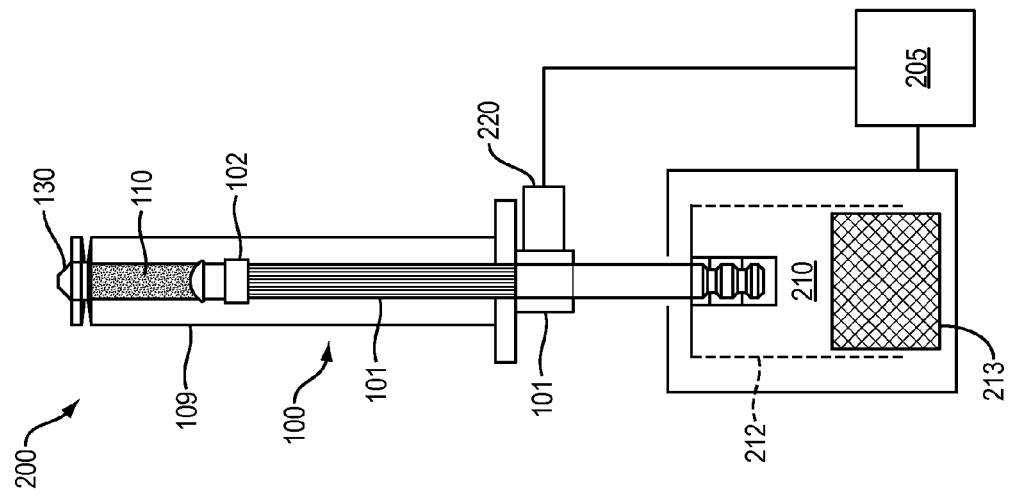
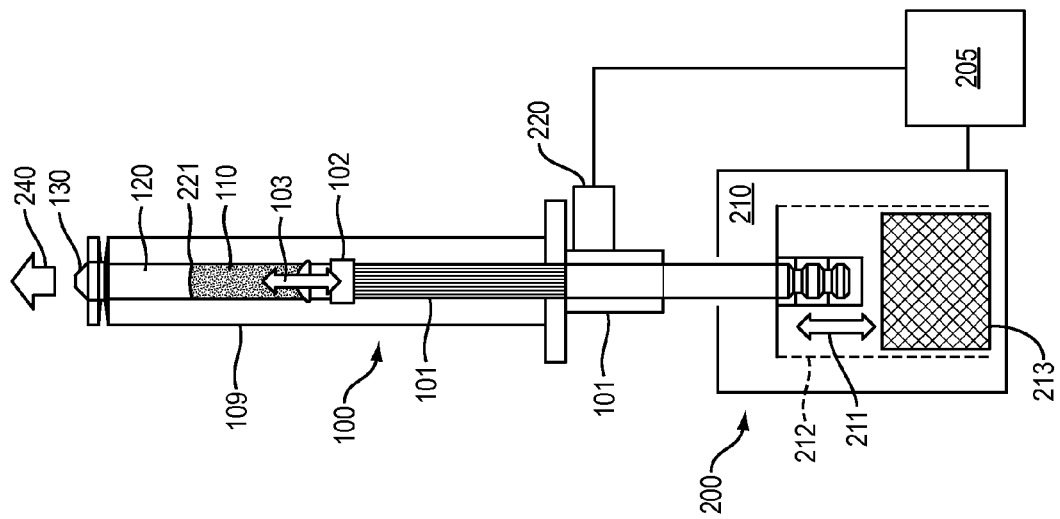

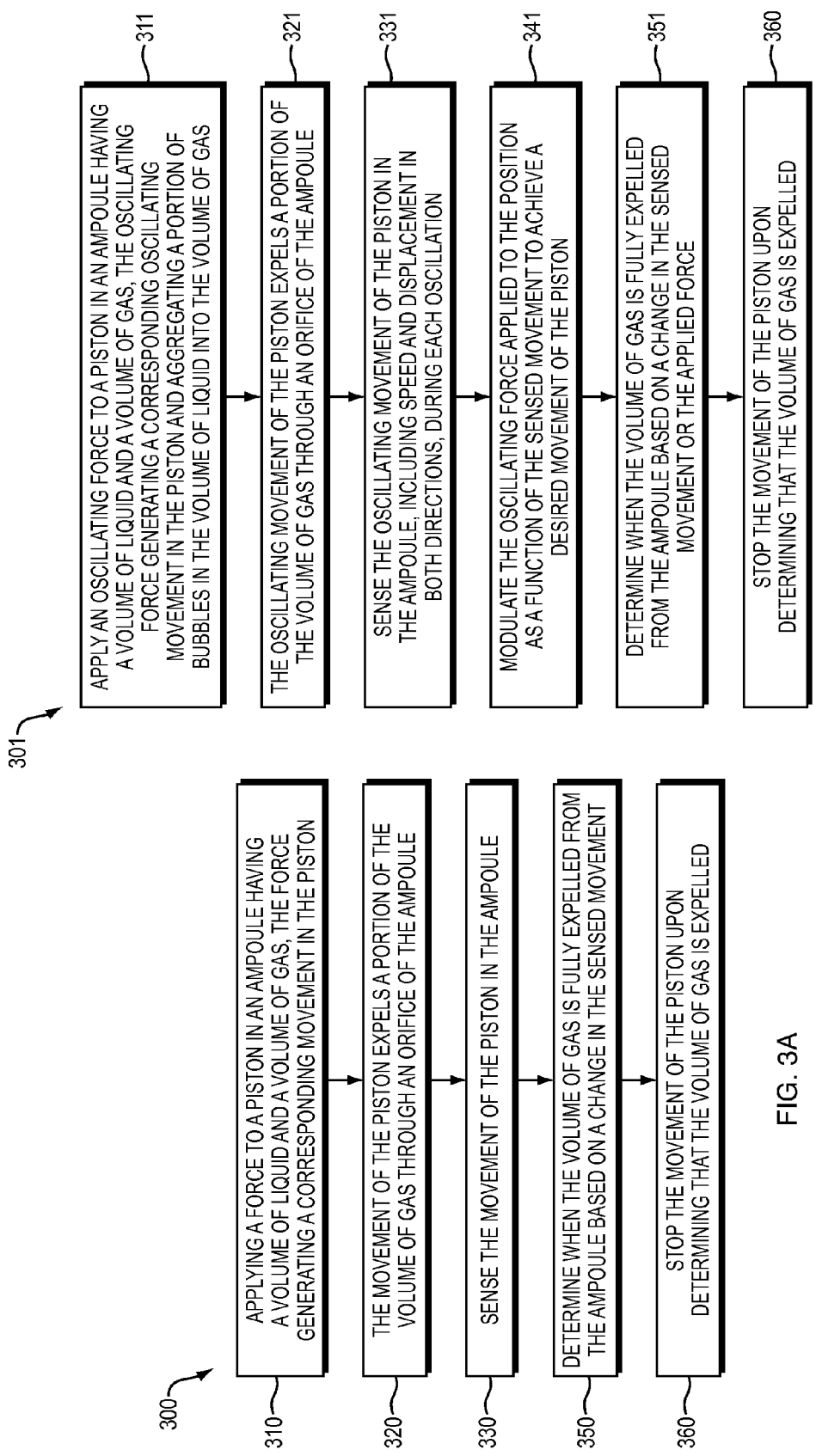

AUTOMATED METHOD FOR SIMULTANEOUS BUBBLE DETECTION AND EXPULSION

RELATED APPLICATION

This application claims the benefit of U.S. Provisional Application No. 61/898,516, filed on Nov. 1, 2013. The entire teachings of the above application are incorporated herein by reference.

BACKGROUND OF THE INVENTION

Injections often require that the fluid of interest be drawn from a vial containing the fluid into a syringe prior to delivery via a needle. Drawing the fluid from the vial can be done using an empty syringe or a syringe filled with a volume of air equal to the desired volume of fluid to be withdrawn. In the latter instance, removal of fluid using an empty syringe is difficult because of the increased pressure within the vial and often results in the withdrawal of air into the syringe and loss of fluid when the needle is withdrawn from the vial. In the former, a small amount of air is drawn into the syringe due to the dead space within the needle itself. In the context of injections for medicinal use, injection of air can be both painful and dangerous to a patient, and current practice involves removal of the bubbles prior to injection. Elimination can be accomplished by flicking the syringe to get the bubbles to pool at the top of the barrel followed by depression of the plunger to expel the air.

Since there is usually no definitive means to determine the exact point at which all air has been evacuated, there is unnecessary loss of fluid as the user must overcompensate in depressing the plunger until a small amount of fluid is expelled from the chamber. Besides the cost of the wasted drug, this process has a few other problems as well. The excess fluid could prove to be harmful if it is absorbed as a result of contact with the skin or mucous membranes. Due to these concerns, the bubble-removal process can be both time consuming and stressful: a user must continuously check the syringe barrel to ensure no air is in the chamber, while moving the plunger slowly enough to ensure minimal fluid loss. Additionally, this process can be time-consuming as the user must check the barrel continuously to determine that no air remains in the barrel.

SUMMARY OF THE INVENTION

Accordingly, there exists a need for an automated method of bubble detection, aggregation, and removal scheme and corresponding apparatus to solve these problems.

An example embodiment of the present invention is a method of detecting and removing air from a syringe containing a volume of liquid and a volume of gas, including moving a piston in the syringe to expel gas through an orifice of the syringe, sensing a movement of the piston in the syringe, and determining when the volume of gas is expelled from the syringe based on a change in the sensed movement. Moving the piston in the syringe may include controlling a force applied by an electromagnetic actuator as a function of the movement of the piston.

In some embodiments, moving the piston includes applying oscillating force to the piston using an actuator, which may be an electromagnetic actuator, and sensing a movement of the piston may include sensing an oscillating movement of the piston in the syringe. The method may include stopping movement of the piston upon determining that the volume of gas is expelled from the orifice and stopping movement of the piston may occur after a forward movement of the piston. In some embodiments, stopping movement of the piston occurs upon determining that the volume of liquid is expelled from the orifice. Determining that the volume of gas is expelled from the orifice may include determining that at least a portion of the volume of liquid is expelled through the orifice.

In some embodiments, applying the oscillating force to the piston includes applying at least one of the following in alternation to the piston: a positive and a negative force, a positive and a zero force, and a first positive force and a second positive force. The oscillating force may have a frequency between 50 Hz and 500 Hz. In some embodiments the oscillating force has a frequency below a cutoff frequency of the piston and syringe when containing the volume of liquid. The frequency of the oscillating force may be below an ultrasonic frequency. The actuator may be a bi-directional Lorentz-force electromagnetic actuator. Sensing the oscillating movement of the piston may include sensing at least one of: displacement of the piston during each oscillation and speed of the piston during each oscillation, and wherein determining when the volume of gas is expelled from the syringe is based on a change in the at least one of displacement and speed of the piston. In some embodiments, sensing the oscillating movement of the piston includes sensing at least one of the following: a forward speed of the piston during each oscillation, a forward displacement of the piston during each oscillation, a backward speed of the piston during each oscillating, and a backward displacement of the piston during each oscillation. Determining when the volume of gas is expelled may be based on a change in the sensed oscillating movement during one or more oscillations of the piston or based on the sensed movement as compared to a given reference value.

In some embodiments, the volume of liquid further includes a plurality of bubbles and the oscillating force applied by the bi-directional Lorentz-force electromagnetic actuator aggregates at least a portion of the plurality of bubbles into the volume of gas.

In some embodiments, sensing the movement of the piston may include sensing a forward speed the piston, and determining when the volume of gas is expelled from the syringe is based on a sensed decrease in the forward speed of the piston.

Another example embodiment of the present invention is an apparatus for detecting and removing air from a syringe including a piston and an orifice. The syringe contains a volume of liquid and a volume of gas disposed in the syringe between the piston and the orifice, the volume of gas being adjacent to the orifice. A position sensor is adapted to sense the movement of the piston in the syringe, an electromagnetic actuator is adapted to move the piston in the syringe and a controller is responsive to the position sensor. The controller causes the electromagnetic actuator to move the piston and drive the one or more bubbles through the orifice and determines when the volume of gas is expelled from the syringe as a function of a sensed change in the movement of the piston. The electromagnetic actuator may be a bi-directional Lorentz-force actuator. In some embodiments, the controller modulates a force applied by the electromagnetic actuator to move the piston as a function of the movement of the piston. The controller may be further configured to stop movement of the piston upon the determination that the volume of gas is expelled from the orifice or upon the determination that a portion of the volume is liquid is expelled through the orifice.

In some embodiments, the electromagnetic actuator is configured to apply an oscillating force to the piston, and the position sensor is further adapted to sense oscillating movement of the piston. The oscillating force may have a frequency between 50 Hz and 500 Hz and the oscillating force applied to the piston by the electromagnetic actuator may be at least one of the following: a positive force and a negative force, a positive and a zero force, and a first positive force and a second positive force. The position sensor may be adapted to sense at least one of: displacement of the piston during each oscillation and speed of the piston during each oscillation, and the controller may determine when the volume of gas is expelled from the syringe is a function of the at least one of displacement and speed of the piston. In some embodiments, the position sensor is further adapted to sense at least one of: a forward speed of the piston during each oscillation, a forward displacement of the piston during each oscillation, a backward speed of the piston during each oscillating, and a backward displacement of the piston during each oscillation. In some embodiments, the change in the sensed oscillating movement is at least one of the following: an increase in the backwards speed of the piston, an increase in the sensed displacement of the piston, a decrease in the forward speed, or a decrease in the forward displacement of the piston. The controller may determine when the volume of gas is expelled as a function of a change in the sensed oscillating movement during one or more oscillations of the piston or a as a function of the change during one or more oscillations as compared to a reference value.

In some embodiments, the volume of liquid includes a plurality of bubbles and the oscillating force applied by the actuator aggregates at least a portion of the plurality of bubbles into the volume of gas.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 1A-C are illustrations of filling a syringe with a volume of liquid from a vial with a small volume of air remaining in the syringe.

FIG. 1D is an illustration of a prior art method of expelling an air bubble from the syringe of FIG. 1B.

FIGS. 2A-B are schematic views of a syringe and bi-directional electromagnetic actuator system of the present invention configured to detect and remove bubbles from the syringe in accordance with an aspect of the disclosed embodiment.

FIGS. 3A-C are flowcharts of methods for detecting and removing bubbles in a syringe in accordance with aspects of the disclosed embodiment.

FIG. 5A includes rubrics for net (A), forward (B) and backward (C) displacement. FIG. 5B includes rubrics for net (D), forward (E), and backward (F) speed.

DETAILED DESCRIPTION OF THE INVENTION

Figure 3C:
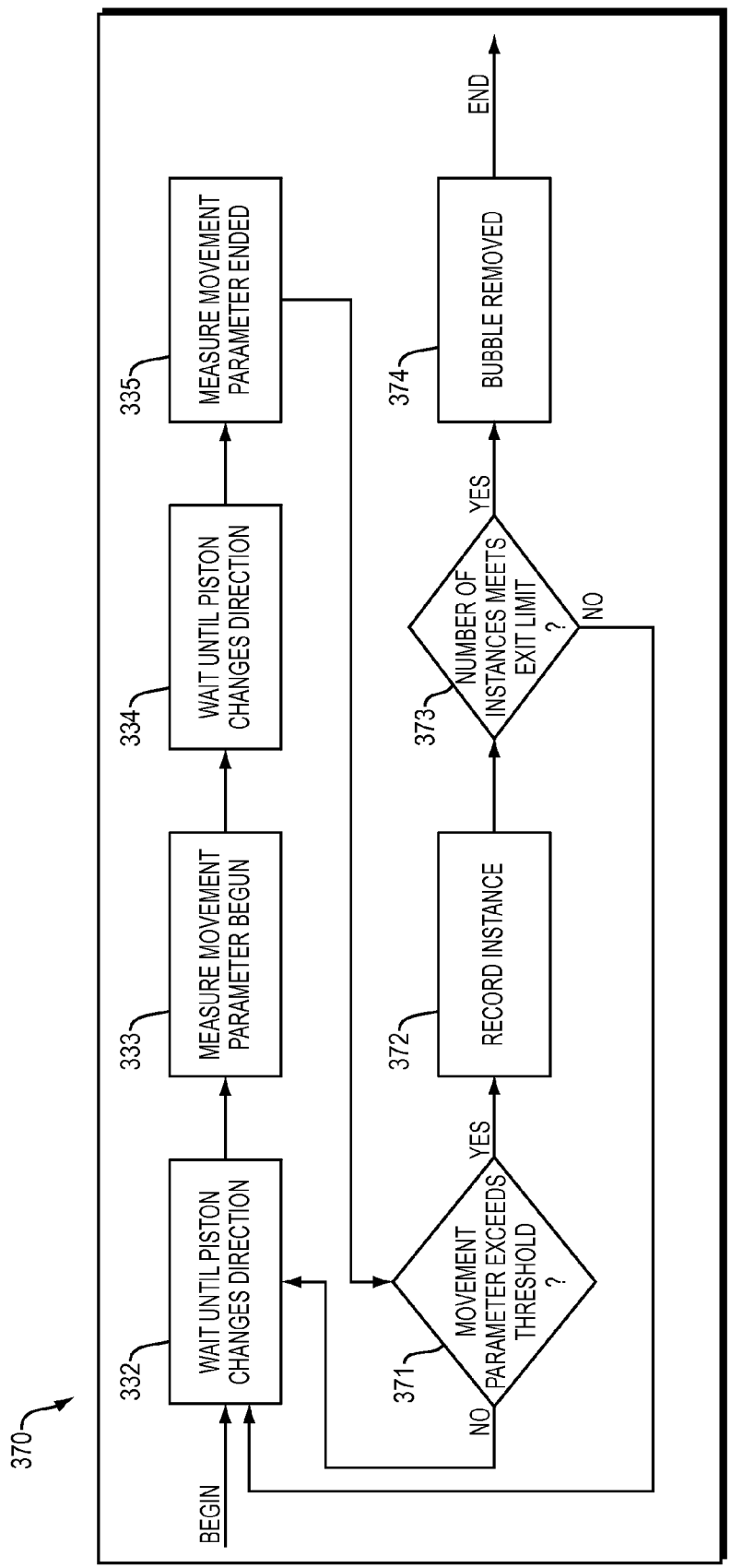

A description of example embodiments of the invention follows.

This disclosure describes an automated method by which liquid bubbles can be aggregated, and then simultaneously detected non-visually and expelled from a syringe or cartridge using a piston that is made to vibrate via a transducer as it is controllably moved in a forward direction. This method provides a simultaneous air bubble detection, and expulsion technique. Disclosed embodiments expedite the entire air expulsion process in a syringe or ampoule compared to current methods. This method could be performed on any process in which a syringe is controlled electronically with a transducer and some position feedback (be it an individual sensor or a self-sensing actuator) is used, without the need for any extra machinery or sensors.

This method provides a simultaneous air bubble detection, aggregation, and expulsion technique, while other air bubble detection methods offer at most a combination of two of these three features. This expedites the entire air expulsion process in a syringe or ampoule compared to current methods. This method could be performed on any process in which a syringe is controlled electronically with a transducer and some position feedback (be it an individual sensor or a self-sensing actuator) is used, without the need for any extra machinery or sensors.

This method could be used in any application in which a syringe is controlled through an actuator, and air bubbles are not desired in the fluid. This could include liquid chromatography or angiography in which a syringe of a desired fluid is injected into a system, or it can also be used in a needle-free injection devices in which the syringe of fluid is drug to be delivered to a patient.

In the typical prior art operation of a syringe there is no definitive means to determine the exact point at which all air has been evacuated from a syringe. As a result, there is often unnecessary loss of fluid for one or multiple possible reasons: (i) a user may overcompensate while depressing the plunger until a small amount of fluid is expelled from the chamber. (ii) a user may not depress the plunger slow enough to accurately cease depression upon evacuation of the air, or (iii), a portion of the air remains in the needle when a small volume of liquid is expelled prior to the remainder of the air. Besides the possibly high costs, in aggregate, of the wasted drug, this process has a few other problems as well. The excess fluid ejected from the syringe may prove to be harmful if it is absorbed as a result of contact with a person's skin or mucous membranes. Additionally, any manual methods or processes of removing air from a syringe can be time-consuming as the user must visually inspect the syringe barrel continuously when in use. Automated bubble detection, aggregation, and removal methods and addresses these problems and improves the efficiency of using a syringe.

Prior art Test Detection of gas bubbles in a fluid has been accomplished in many ways. Acoustic resonance/ultrasonic detection or optical refraction techniques are often used as a more "remote" way of measuring the presence of air bubbles [1]. However, for the application of bubble detection in a syringe, these prior art methods and systems require unnecessary equipment to detect the presence of an air bubble and are generally used to only signal the presence of an air bubble [2] rather than provide an inherent means to aggregate these bubbles and remove them.

Test Mechanical means have also been used in the past to detect the presence of gas bubbles in a fluid [3, 4, 5, 6]. In these prior art methods and systems, changes in the mechanical properties of a fluid when gas is introduced, namely compressibility and response to pressure oscillations are actively monitored. A possible benefit of the prior art mechanical systems is that sometimes a preexisting transducer in the system may be used as the means to excite the fluid as well as potentially sense the desired result; however, these prior art solutions require measurement of the mechanical properties when the fluid is in a sealed container, restricting their use to systems that cannot actively expel bubbles from the fluid while they are being detected.

A non-visual method and apparatus for determining the presence of liquid bubbles in a syringe while expelling them is disclosed.

FIGS. 1A-C are illustrations of filling a syringe with a volume of liquid from a vial, with a small volume of air remaining in the syringe. FIGS. 1A and 1B shows a syringe 100 attached to a vial 10 by way of a vial adaptor 20. The syringe 100 includes a syringe barrel 109, also referred to as an ampoule, containing an internal piston 101 with a piston head 102 in fluid communication with an orifice 130 at a distal end of the syringe barrel 109. The piston 101 is drawn backwards with a force 9 and the corresponding movement of the piston head 102 draws a volume of fluid 110 from the vial 10, though the orifice 130, and into the syringe. Subsequently, as shown in FIG. 1B, the syringe 100 is removed from the vial adaptor 20 and contains a small volume of air 120 in addition to the volume of liquid 110. Inversion and perturbation, e.g., tapping with a fingertip, of the syringe 100, shown in FIG. C, permits the volume of air 120 to rise to a distal end of the syringe 110 where it is positioned in fluid communication with an orifice of the syringe 100. Prior art methods for removal of this volume of air 120, as shown in FIG. 1D, include applying a force 99 to the piston 101 of the syringe 100 to drive the volume of air (not shown) through the orifice 130 until an observable volume of liquid 199 is expelled though the orifice 130 of the syringe 100.

FIGS. 2A-B are schematic views of a syringe and bi-directional electromagnetic actuator system configured to detect and remove bubbles from the syringe in accordance with aspect of the disclosed embodiment. FIG. 2A shows apparatus for automated bubble detection and elimination 200 including a syringe 100 having syringe barrel 109, or ampoule, filled with the volume of liquid 110 and the volume of air 120. The volume of liquid 110 may be, for example, a liquid medicament. The ampoule 109 contains the piston 101 with attached piston head 102 in fluid communication with the volume of liquid 110 is tilted upwards, allowing the volume of air 120, also referred to as one or more bubbles or air bubbles, to aggregate to the ampoule orifice 130. The apparatus for automated bubble detection and elimination 200 also includes an actuator 210 coupled to the piston 101 of the syringe 100 and configured to apply a force 211 to the piston 101 and generate a corresponding movement 103 of the piston head 102. The apparatus for automated bubble detection and elimination 200 also includes a position sensor 220 and a controller 205. The position sensor 220 may be, for example, integrated with the syringe 100 to measure a position of the piston 101 directly, or integrated with the actuator 210 to measure a position of a drive component (not shown) of the actuator 210. The position sensor 220 may be configured to sense, for example, position, speed, or displacement of the piston 101 at a given frequency. The controller 205 is in electrical communication with the position sensor 220 and controls the actuator's 210 application of force 211 to the piston 101.

The actuator 210 may be an electromagnetic actuator, a piezoelectric actuator, or a bi-directional electromagnetic actuator configured to apply oscillating positive and negative forces to the piston. In FIGS. 2A-B the actuator 210 is shown as a bi-directional Lorentz-force electromagnetic actuator 210 including a moving coil 212 surrounding a permanent magnet 213, the coil configured to contain a current moving perpendicularly to a magnetic field of the magnet 213 and generate a force 212 linearly responsive to the strength of the current in the coil 212. The Lorentz-force actuator 210 is particularly suited to provide the precise control over both force and position of the piston 101, necessary to detect and remove the volume of air 120 without expelling any of the volume of liquid 110. A Lorentz-force actuator is described in more detail in U.S. Pat. Nos. 8,172,790 and 7,833,189, the teachings of which are herein are incorporated by reference in their entirety.

Generally, the force 211 applied to the ampoule 109 when it contains a volume or liquid 110 or a volume of liquid 110 and a volume of air 120 causes a substantial restoring or opposing force against the piston 101 in a direction opposite to the applied force 211. Specifically, as shown below, the restoring force of an ampoule containing a volume of liquid 110 and a volume of air 120 changes suddenly when the volume of air 120 is fully discharged from the ampoule 109. Embodiments of the present invention include sensing various movement parameters of the piston 101 as an applied force 211 expels the volume of air 120 and determining, based on the sensed position of the piston 101, when the restoring force changes as a result of the volume of air 120 being fully expelled. An oscillating applied force 211 may provide a higher and lower (or negative or zero) force in alternation in order to 'load' or pressurize the ampoule 109 during the higher applied force and permit the force restoring force generated in response to the higher applied force to momentarily affect the movement of the piston 101 more strongly when applied force is lowered. The oscillating force 211 configuration may maximize the ability of the position sensor 205 to resolve to resolve the effect of the restoring force changing after the discharge of a volume of air 120 from the ampoule 109. In some embodiments, for example, and described in more detailed in FIG. 5A, the backwards displacement of the piston 101 during each of the lower applied oscillating forces is measured and compared to a known threshold value for the displacement of a similar ampoule in a fluid-only condition to determine when the measured ampoule contains only the volume of liquid 110.

Another advantage of an oscillating applied force 211 are facilitating aggregation of any bubbles present in the volume of liquid 110 and preventing static friction or stiction from affecting the movement, provided that the frequency of the oscillations is chosen high enough to prevent any momentary stoppage of the piston head 102 from forming an intra-molecular bond between the piston head 102 and an inner wall of the ampoule 109.

Figure 5A:
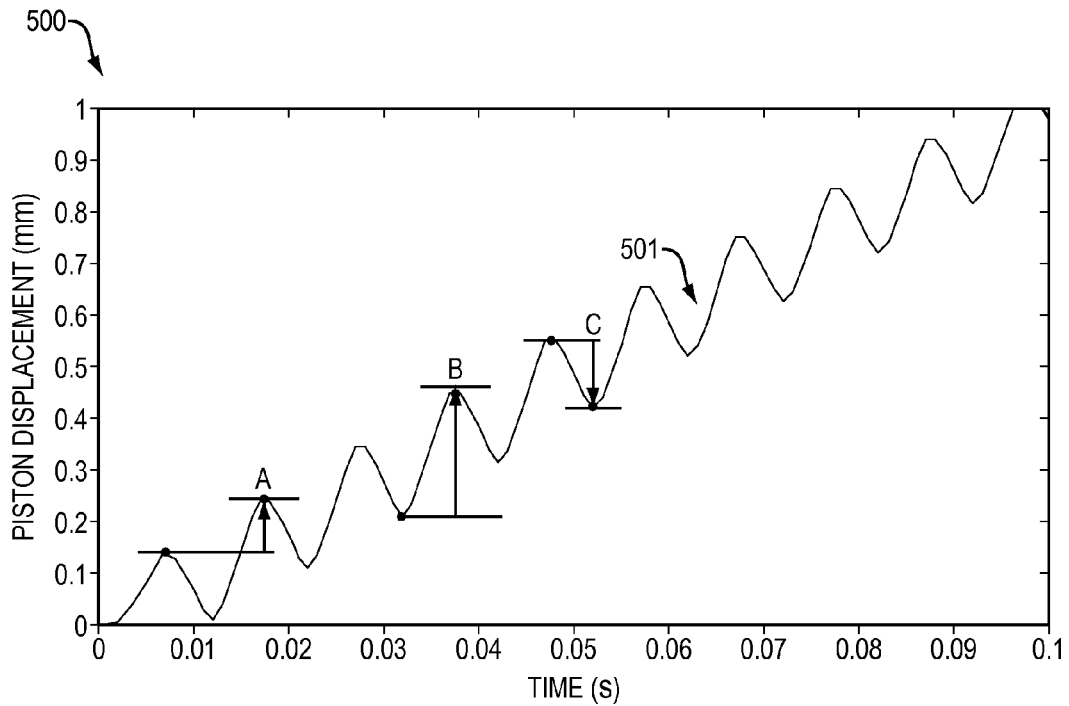
FIGS. 5A-B are graphs of position of a piston in a syringe with an oscillating force applied to the piston.
Figure 5B:
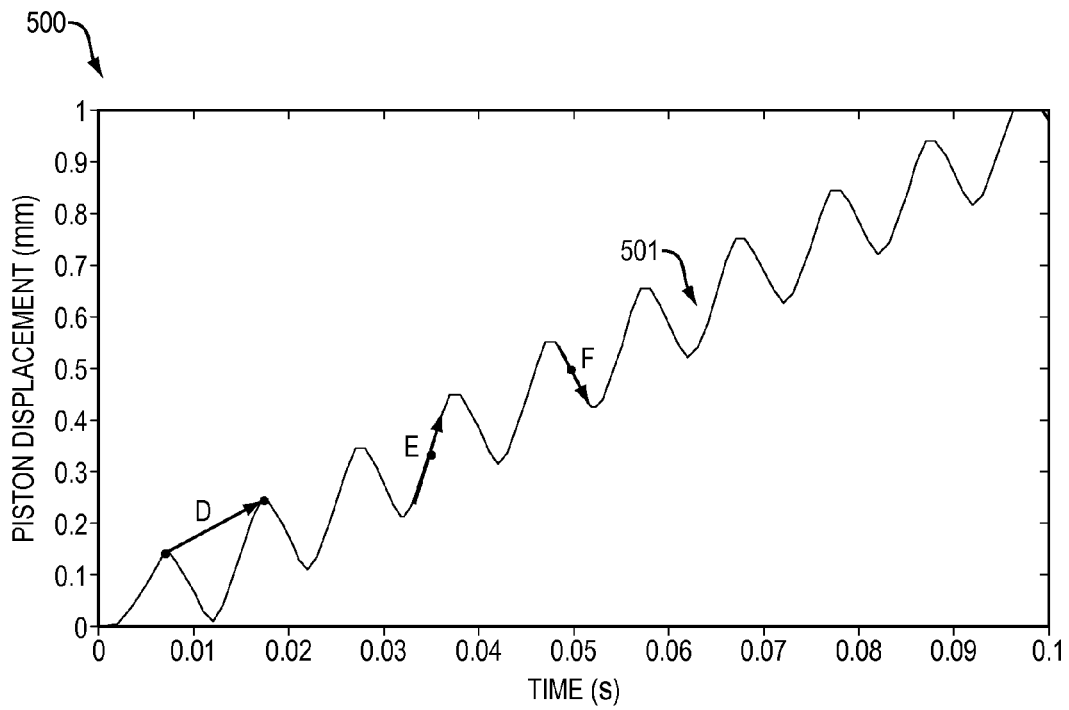

FIGS. 5A-B are graphs of position of a piston in a syringe with an oscillating force applied to the piston and includes rubrics for net (A), forward (B) and backward (C) displacement, and net (D), forward (E), and backward (F) speed. FIG. 5A shows a piston displacement vs. time plot 500 of an oscillating piston position signal 501 of a typical ampoule 109 and piston 101 combination as described above and driven by a force on the ampoule 109 oscillating between a positive and negative value, with a positive average value. The calculation of the three displacements measurements, i.e., net (A), forward (B), and backwards (C), used in the subsequent displacement figures is now described. Net displacement (A) is measured as the piston displacement between subsequent peaks in the oscillating piston position 501. In some embodiment, the piston position 501 may not move in a negative direction between oscillations, as shown in plot 500, and the net displacement measured is determined by inflections in the piston position 501 corresponding to changes in the applied force 211. Continuing, forward displacement (B) is measured as the piston displacement between a trough and valley, as shown, and represents the total forward piston movement (towards orifice 130) during each oscillation of the piston position 501. Backwards displacement (C) is measured as the piston displacement between a valley and a trough, as shown, as represents the total backwards piston movement during each oscillation. Again, alternatively, if the applied force 211 oscillates between two positive values, there may be no backwards displacement, in which case a second, smaller, calculated forward displacement of the piston position 501 is measured.

FIG. 5B shows the calculation of the three speed measurements, i.e., net (D), forward (E), and backwards (F), used in the subsequent speed figures. Net speed (D) is defined as the net displacement divided by the time between the corresponding peaks. Forward speed (E) is defined as the slope of the piston position 501 as the piston 101 moves toward the orifice 130 of the ampoule 109, and backwards speed (F) is defined as the slope of the piston position 501 as the piston 101 moves away from the orifice 130 of the ampoule 109. Again, alternatively, if the applied force 211 oscillates between two positive values, there may be no backwards speed, in which case a second, smaller, calculated forward speed of the piston position 501 is measured.

In operation, the actuator 210 applies a force 211, e.g., an oscillating force, to the piston 101 and moves the piston 101 and attached piston head 102 towards the orifice 130 of the ampoule 109 to expel the volume of air 120 through the orifice 130. Additionally, if an oscillating force 211 is applied to the piston 101, the oscillating movements of the piston head 102 may induce bubble aggregation by freeing one or more bubbles (not shown) present in the volume of liquid 110 and attached to the side of the ampoule 109 to break free of the ampoule 109 and rise into the volume of air 120. In operation, prior to any net forward movement of the piston 101, a stationary oscillating force, i.e., a force oscillating about 0, may be applied to the piston 101 by the actuator 210. Continuing, after a set amount of stationary vibration, the piston 103 is oscillated with a positive oscillating force, i.e., a force oscillating about a positive value (where a positive force is in a direction towards the orifice 130), is applied to the piston to move the piston head 102 toward the end of the ampoule 109 and expel the volume of air 120 through the orifice 130 of the ampoule 109 as the piston head 120 moves forward.

During the movement of the piston 101 by the actuator 210, the position sensor 220 senses the position of the piston head and the controller 205 uses the sensed positions of the piston 101 during the movement of the piston 101 to determine when the volume of air 120 has been expelled from the ampoule 109, as shown in FIG. 2B. The position of the piston 101 may be recorded by the controller 205 as the piston 105 is oscillated or moved, either through the separate position sensor 220 or a self-sensing technique using a feedback from the actuator 210. Through the recorded position readings, the controller determines a shift from an air-fluid mixture in the ampoule 109 to a fluid only mixture in the ampoule 109, i.e., when the volume of air 120 is expelled from the ampoule 109. The controller may determine the transition to a fluid-only condition in the ampoule 109 in different ways, including the following: (i) The average velocity of the piston 101 moving forward (toward the ampoule 109 orifice 130) decreases, (ii) The forward displacement of the piston 101 during each oscillation decreases, or (iii) The backward displacement of the piston during each oscillation increases.

A change in the volume elasticity of the fluid 110 and air 120 mixture, the elimination of an air-water-ampoule interface (a meniscus 221), or a combination of both may cause the changes mentioned above. Volume elasticity theory explains that the volume of liquid 110 has a significant push-back (or restoring force) on the piston 110 as it moves backward, while a fluid-air mixture will exert a lower restoring force on the piston. Additionally the presence of an air-water-ampoule interface implies the presence of a meniscus 221. Moving the piston backwards or forwards when an air-fluid mixture is present may stretch this meniscus 221 and resist any movement of the piston, and this meniscus effect is not present once the volume of air 120 is expelled from the ampoule 120. Additionally, when the piston 101 is pushed forward against the fluid-air mixture 110, 120 in the ampoule 109 of FIG. 2A, the volume of air 120 exits the ampoule 109 orifice 130 first and, as a result of a significantly higher compressibility and lower viscosity as compared to the volume of liquid 110, the volume of air 120 exits the orifice 130 with little resistance compared to the volume of fluid 110, which is generally incompressible when compared to the volume of air 120. Any combination of these effects may produce a measureable change in the sensed position of the piston 101 as the volume of air is expelled. The changes may be used by the controller 205 to determine whether the volume of air 120 is present in the ampoule 109 or not, i.e., when the volume of air 120 is fully expelled from the ampoule 109 as shown in FIG. 2B.

FIGS. 3A-C are flowcharts of methods for detecting and removing bubbles in a syringe in accordance with aspect of the disclosed embodiment. FIG. 3A is a method for automatic detection open-loop and removal of a volume of air 120 from an ampoule 109 of a syringe 100 including the following steps. At step 310, a force 211 is applied to the piston 101 in the syringe 100 having the volume of liquid 110 and the volume of gas 120, the force 211 generating the movement 103 in the piston 101. At step 320, the movement 103 of the piston 101 expels a portion of the volume of air 120 though the orifice 130 of the syringe. At step 330, the movement of the piston 101 in the ampoule 109 is sensed. At step 350, when the volume of air 120 is fully expelled from the ampoule 109 is determined based on a change in the sensed movement of the piston 101. At step 360, the movement 103 of the piston 101 is stopped upon the determination that the volume of air 120 is expelled from the ampoule 109.

FIG. 3B is a method embodiment for automatic closed-loop detection and removal of a volume of air 120 from an ampoule 109 of a syringe 100 including the following steps: At step 311, apply the oscillating force 211 to the piston in the ampoule having the volume of liquid 110 and the volume of gas 120, the oscillating force generates a corresponding oscillating movement in the piston 103 and, may aggregate a portion of bubbles in the volume of liquid 110 into the volume of gas 120, if present. At step 321, the oscillating movement of the piston 103 expels a portion of the volume gas 120 though the orifice 130 of the ampoule 109. At step 331, the oscillating movement 103 of the piston 101 in the ampoule 109 is sensed, including a speed and displacement in both directions (forward and backward), during each oscillation. At step 341, the oscillating force 221 applied to the piston 101 is modulated by a controller as a function of the sensed oscillating movement 103 to achieve a desired movement of the piston 101. At step 351, when the volume of gas 120 is fully expelled from the ampoule 109 is determined based on a sensed change in the movement 103 or a change in the applied force 221 and returning to step 311 until the volume of gas 120 is fully expelled from the ampoule 109. At step 360, the movement of the piston 103 is stopped when the volume of gas 120 is determined to be fully expelled from the ampoule 109.

FIG. 3C is an example embodiment of a method embodiment for determining if the volume of air 120 is fully expelled from the ampoule 109 based on a sensed movement of the piston 101. The sensed movement may be, for example, backwards, forwards, or net displacement for each oscillation, and forward, backwards, or net speed during each oscillation. The method includes, at step 332, waiting until the piston 101 changes direction, or otherwise transitions between two sequential oscillations. At step 333, measurement of a movement parameter is started. At step 334, wait until the piston 101 stops, changes direction again, or otherwise transitions to a subsequent oscillation. At step 335, the measurement of the movement parameter is ended. At step 371, if the measured movement parameter is over a given Threshold value, e.g., −0.15 mm for backward displacement, is determined. If no, return to step 332 to measure the next backwards displacement. If yes, at step 372, record or count the instance, and, at step 373, check if the number of recorded instances meets a predetermined detection limit, e.g., 2 consecutive instances. If no, return to step 332 to measure the next movement parameter. If yes, it is determined that the volume of air 120 is fully expelled from the ampoule 109. Provided that the piston 101 is moved by a fast actuator 210 and that the force oscillation are of a small magnitude, the piston 101 can be stopped quickly to ensure minimal loss of fluid once it is determined that the volume of air 120 is fully expelled from the ampoule 109. Sample tests have shown this fluid loss to be on the order of 0.5 to 1.0 microliter for a Lorentz-force actuator 210 as detailed above.

Specifically, for example, the algorithm 370 of FIG. 3C could run until a peak backward speed was less than −42 mm/s, i.e., a speed only reached by the system in a liquid-only condition. The threshold may also be based on a measured change in backward/forward displacement/speed from each oscillation or the threshold may be based on any measured changes identifying the system as being in a liquid-only condition. In an example case, the algorithm may detect when the backward displacement has changed by 20 microns or more in the negative direction. This is a robust way to implement the algorithm of FIG. 3C because it allows for slight differences in the friction of a piston/ampoule set up, but is still dependent on the volume of liquid 110 that is in the ampoule 109. Generally, for any type of force waveform, either the raw values of position/speed, or the change in the values of position/speed are monitored by the position sensor 220. Preferably, for either condition, prior knowledge of how much to expect those values to change during and after the volume of air is removed is needed to distinguish a bubble-expulsion event from other sources of noise in a given system. However, as shown below, a change in the piston 101 position caused by the expulsion of the volume of air 120 can be distinguished from errors/noise across a wide range of force waveforms and liquid to air ratios for typical ampoule 109 and orifice 130 sizes using the algorithm of FIG. 3C with one or more pre-determined threshold parameter determined from measuring the movement parameters when an oscillating force is applied to a liquid-only condition of a given ampoule and orifice syringe device.

Although a best performing choice of force amplitude and force frequency, also referred to as the force waveform, may be heavily dependent on the electromechanical response of the system, the ideal frequency should be one right before the cutoff frequency of the mechanical system (so that the position signal is not being attenuated, and thus harder to measure), while the ideal force should be one that just overcomes the static friction of the device. Both the threshold value and instance limits should be set as "tight" as possible, i.e., the threshold should be just under/above a given system's displacement response of a fluid-only condition, and the instance limit should be set before false positives are possible, i.e., the algorithm stops before it has expelled the bubble.

Figure 4A:
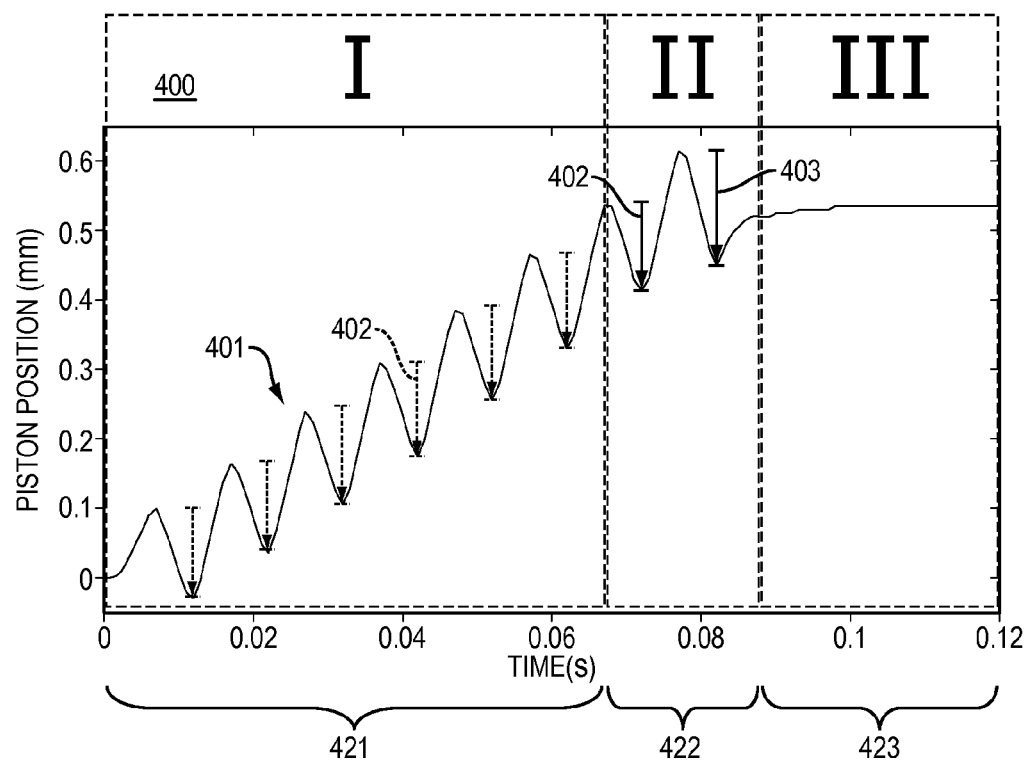
FIGS. 4A-B are graphs of position of a piston and force applied to the piston before, during, and after bubble removal in accordance with an aspect of the disclosed embodiment.
Figure 4B:
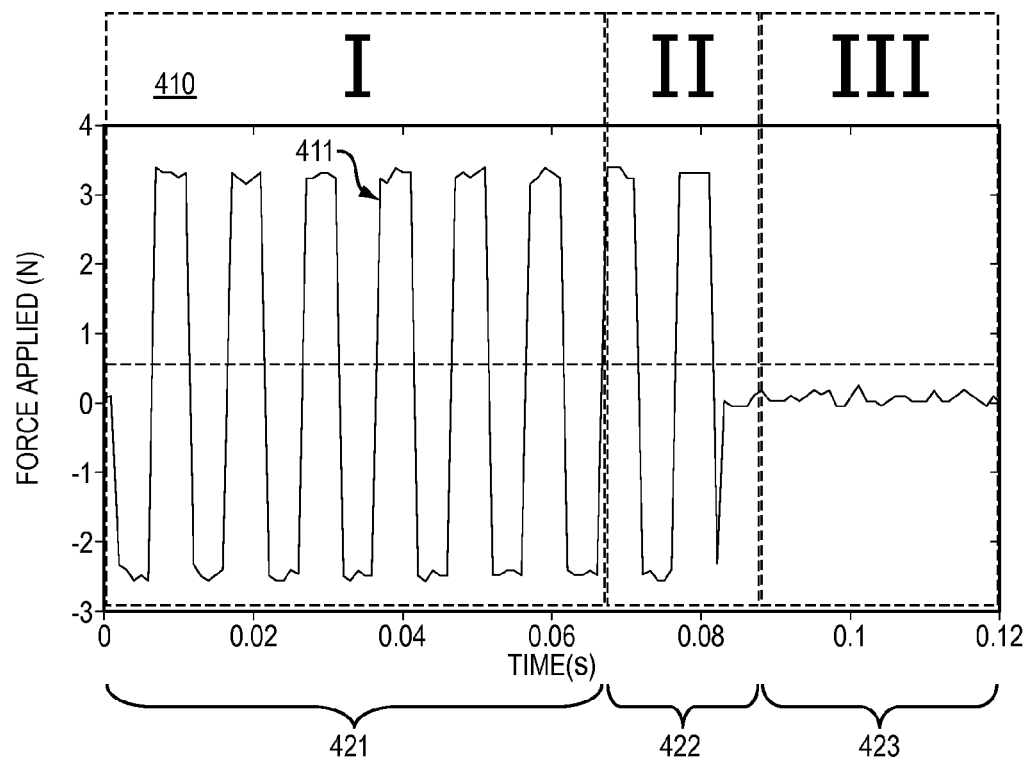

FIGS. 4A-B are graphs of position of a piston and force applied to the piston before, during, and after bubble removal in accordance with aspect of the disclosed embodiment. FIG. 4A shows a position vs. time graph 400 of position 401 of a piston 101 in an ampoule 109 with respect to time. The piston 101 is driven by the oscillating force 411 shown in the force vs. time (or waveform) graph 410 in FIG. 4B. In FIG. 4A, the backwards displacement 402 of the position 401 of the piston 101 is measured during an initial time period 421 to be under a preset threshold value. In the detection time period 422, an increased backwards displacement 403 is measured to be above the threshold indicating, for this particular system, that the volume of air 120 has been expelled. In the final time period 423, the force 411 is reduced to a nominal value to stop any movement of the piston after the determination that the volume of air 120 is expelled.

Figure 6A:
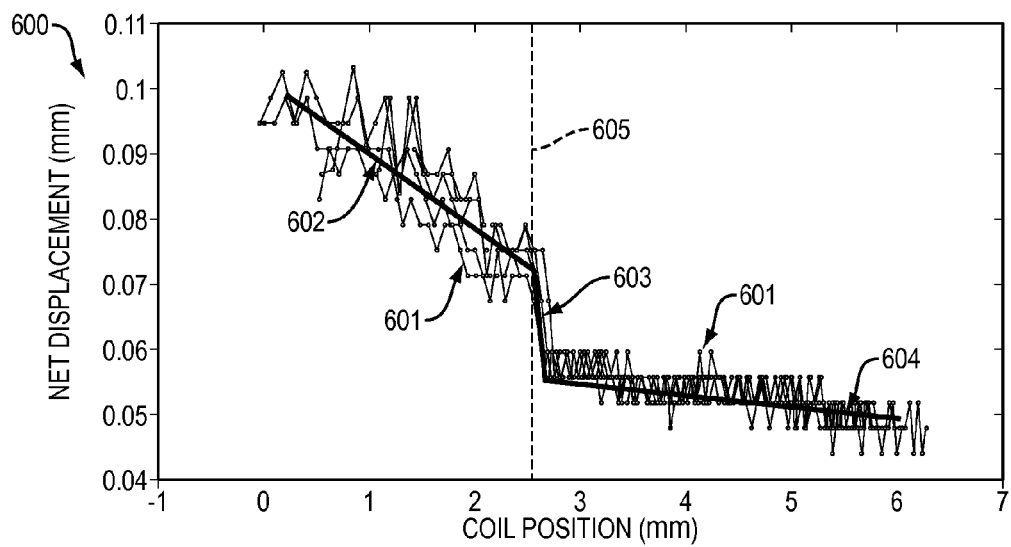
FIGS. 6A-C are graphs of net, forward, and backward displacements, respectively, of a piston in a syringe prior to and after removal of a volume of air in the syringe, with an oscillating force applied to the piston in accordance with aspect of the disclosed embodiment.
Figure 6B:
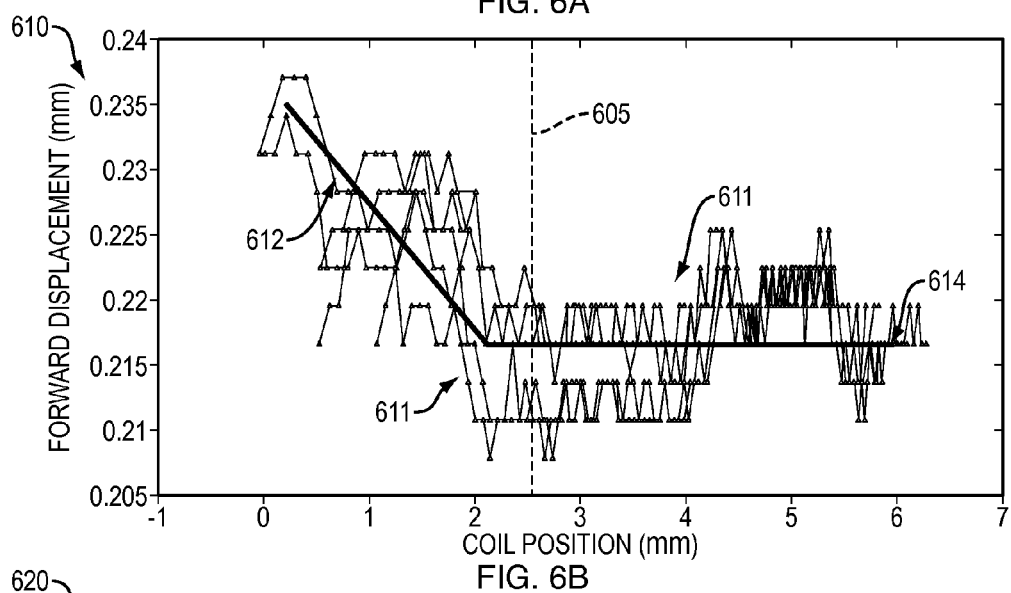
Figure 6C:
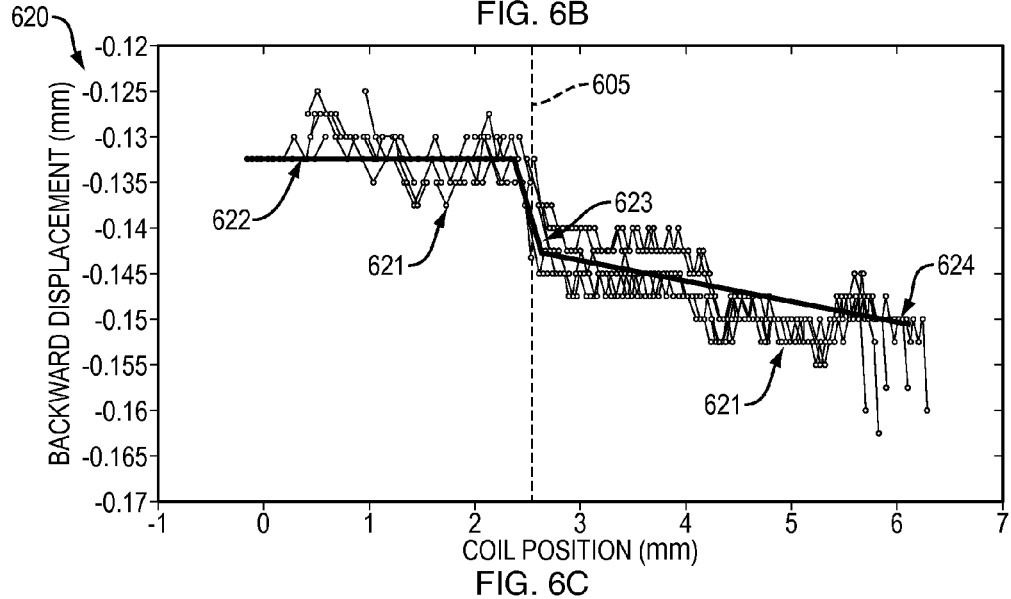
Figure 7A:
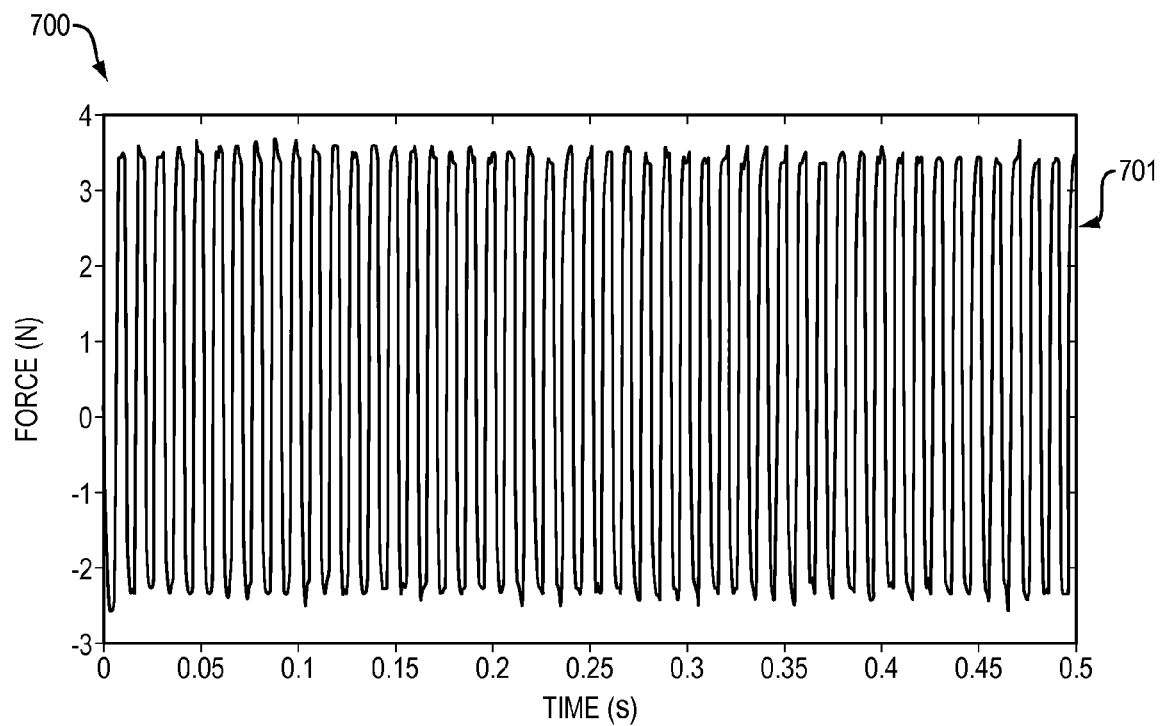
FIGS. 7A-B are graphs of force and position, respectively, of a piston moving in a syringe having a volume of liquid and a volume of air, where the force is oscillating between a positive value and a negative value, in accordance with an aspect of the disclosed embodiment.

FIGS. 6A-C are graphs of net, forward, and backward displacements, respectively, of a piston in a syringe with an oscillating force applied to the piston and includes best-fit lines placed prior to and after observed removal of a volume of air in the syringe to show the presence of a detectable shift in the displacement data corresponded to the volume of air 120 being fully expelled. FIGS. 6A-C shows five displacement plots for a 3 mm inner diameter ampoule having a 200 micron orifice and a 300 microliter volume, a 100 Hz oscillating force applied (as shown in FIG. 7A), and air-to-liquid ratios in the ampoule between 0.017 and 0.36. Additionally, in FIGS. 6A-C, the x-axis of each of the air-to-liquid ratios is shifted to align the removal of the volume of air in the ampoule. FIG. 6A is a plot of net piston displacement 601 for five different air-to-liquid ratios. Best-fit lines are placed before 602, during 603, and after 604 the observed bubble removal 605. FIG. 6B is a plot of forward piston displacement 611 for five different air-to-liquid ratios. Best-fit lines are placed before 612 and after 614 the observed bubble removal 605. FIG. 6C is a plot of backward piston displacement 621 for five different air-to-liquid ratios. Best-fit lines are placed before 622, during 623, and after 624 the observed bubble removal 605. The bubble detection thresholds for similar setups, such as those presented in FIGS. 8A-C and 9A-C, may be used on one or more of the best-fit lines 602, 603, 604, 612, 614, 622, 623, and 624 depending on a quality of each measured displacement direction.

Figure 7B:
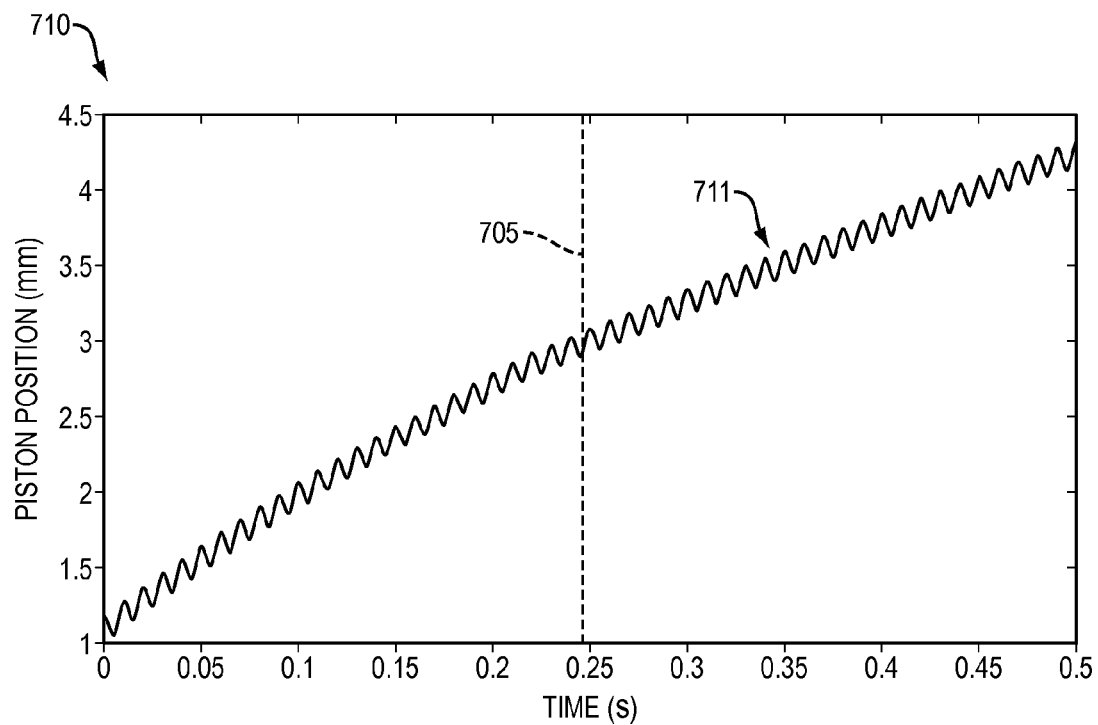

FIGS. 7A-B are graphs of force and position, respectively, of a piston moving in a syringe having a volume of liquid and a volume of air, where the force is oscillating between a positive value and a negative value, in accordance with aspect of the disclosed embodiment. FIG. 7A is a force vs. time graph 700 of the force 701 applied to the pistons of FIG. 7B, FIGS. 8A-F, and FIGS. 9A-F. In FIG. 7A the force 701 oscillates at 100 Hz between a positive and negative value, 3.5 and −2.5, respectively. FIG. 7B is a position vs. time graph 710 of piston position 711 of a piston 101 in an ampoule 109 having a volume of air 120 and a volume of liquid 110 and a force 211 applied according to FIG. 7B. An inflection point 705 in the piston position 711 can be observed around time 0.25 seconds, which represents an observed expelling of the volume of air 120 from the ampoule 109. Although the inflection point 705 is difficult to observe due to the scale of the plot 710, the displacements and speeds during each oscillation of the piston position 711, as calculated with the data selection method of FIGS. 5A-B, are plotted in FIGS. 8A-F.

FIGS. 8A-F are graphs of the net, forward, and backward displacements and net, forward, and backwards speeds, respectively, of the piston position 711 of FIG. 7B showing the detected removal of the volume of air 120 in accordance with the disclosed embodiment. FIGS. 8A-F show that the individual displacement and speed components of the piston position 711 prior to and after the discharge of the volume of air 120 at time 705 enable selection of threshold values for displacement or speed which occur at the time of the inflection point 705 and, as a result, may be into an algorithm, such as the one shown in FIG. 3C, to detect the removal of the volume of air 120 from the ampoule 109 in real-time as the piston 101 moves in the ampoule 109.

Figure 8A:
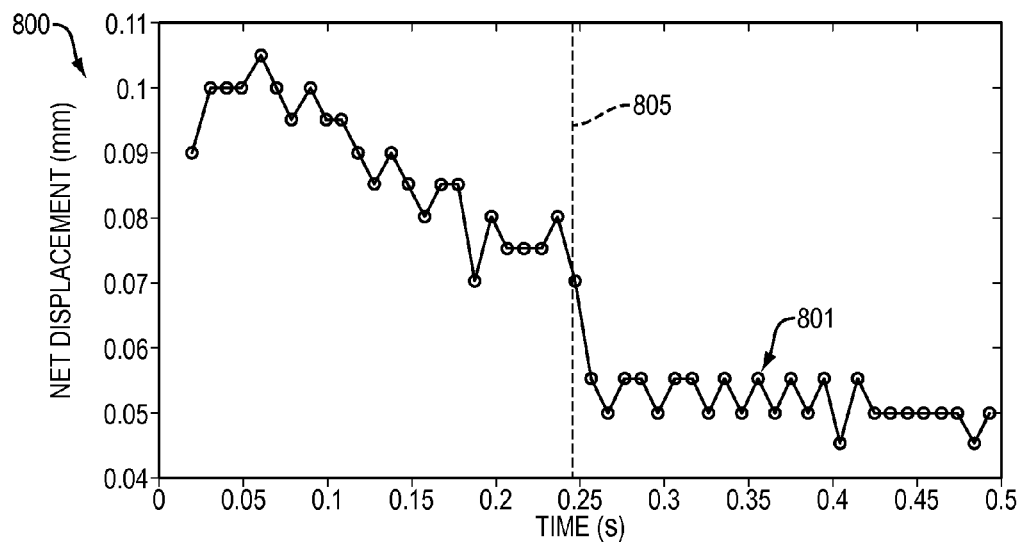
FIGS. 8A-F are graphs of the net, forward, and backward displacements and net, forward, and backwards speeds, respectively, of the piston position of FIG. 7B showing the detected removal of the volume of air in accordance with aspect of the disclosed embodiment.
Figure 8B:
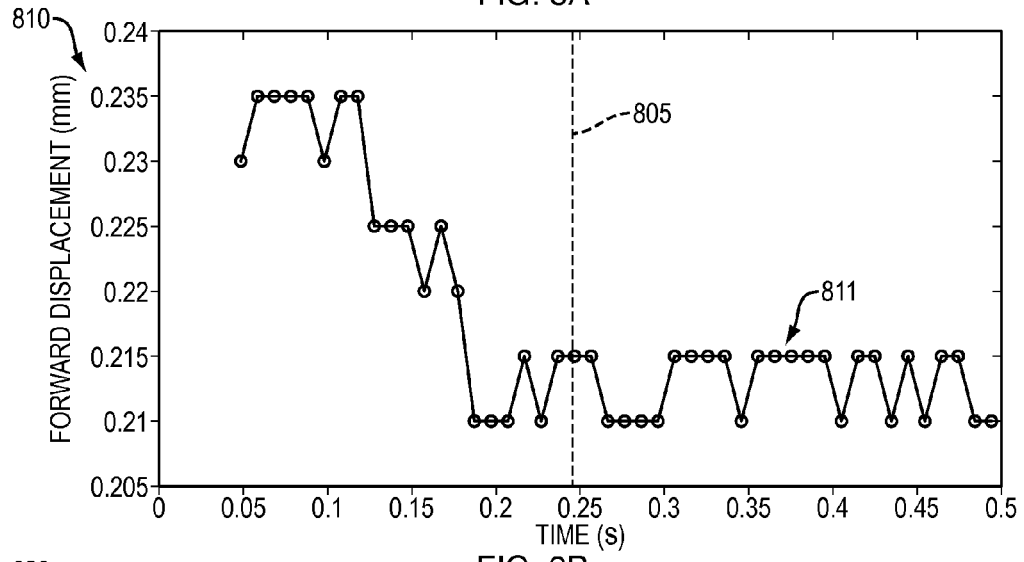
Figure 8C:
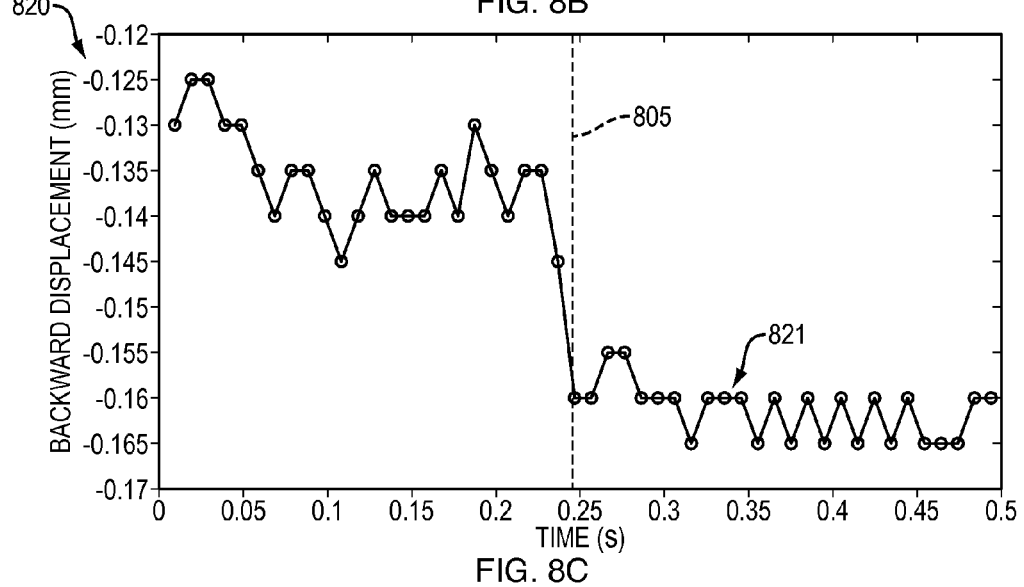
Figure 8D:
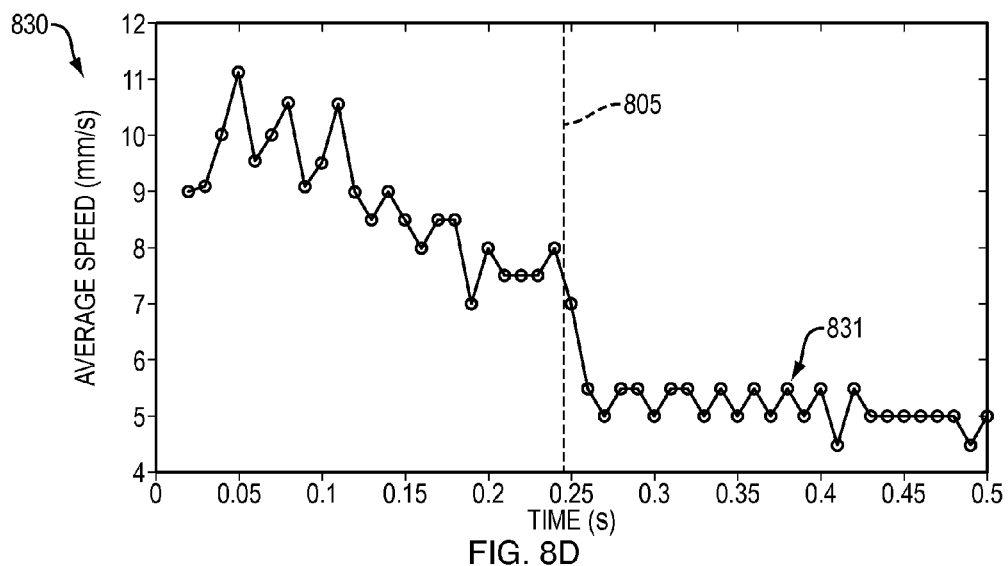
Figure 8E:
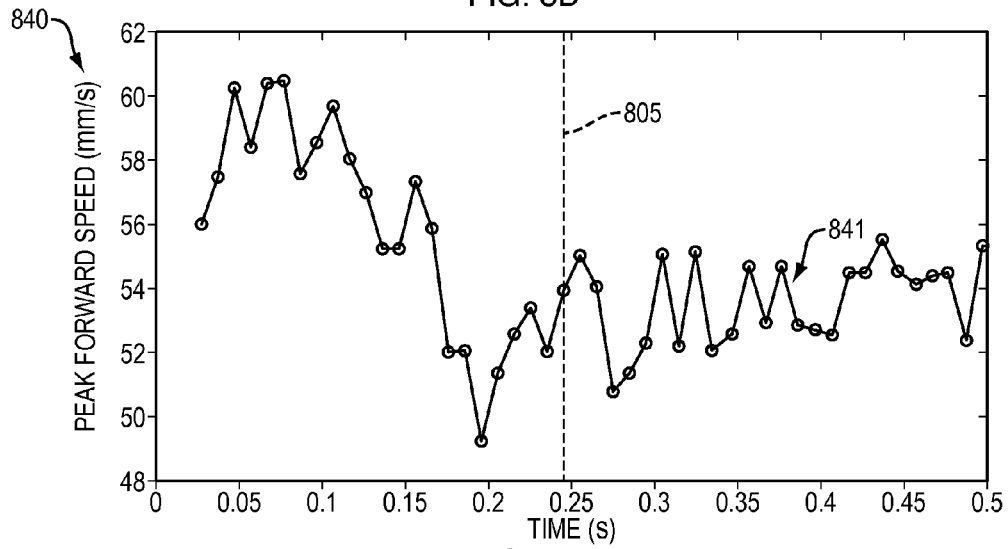
Figure 8F:
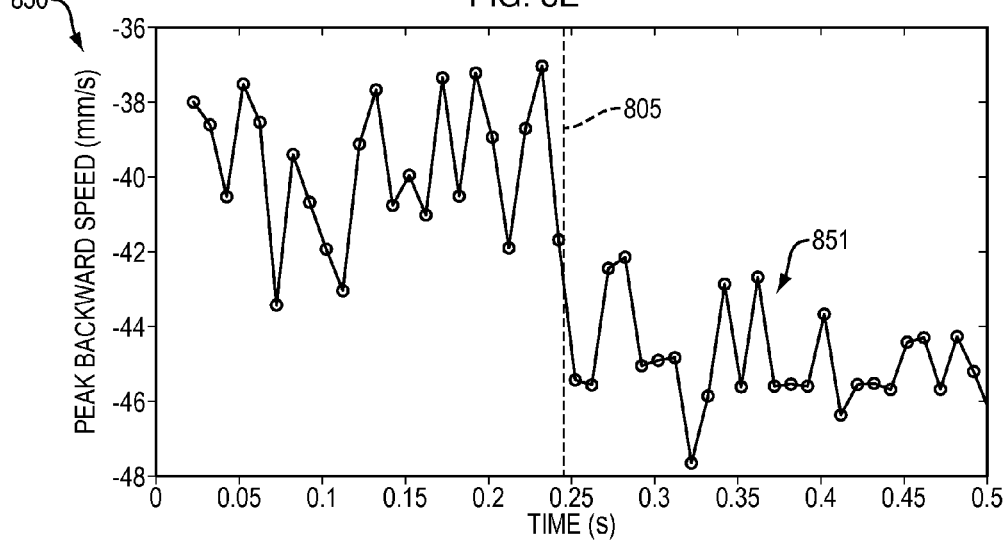

In FIGS. 8A-F, the detected bubble removal time 805 is marked and based on a backwards displacement threshold of −0.15 mm. FIG. 8A is a displacement vs. time plot 800 of the net piston displacement 801 of the piston position 711. FIG. 8B is a displacement vs. time plot 810 of the forward piston displacement 811 of the piston position 711. FIG. 8C is a displacement vs. time plot 820 of the backward piston displacement 821 of the piston position 711. FIG. 8D is a speed vs. time plot 830 of the net piston speed 831 of the piston position 711. FIG. 8E is a speed vs. time plot 840 of the forward piston speed 841 of the piston position 711. FIG. 8F is a speed vs. time plot 850 of the backward piston speed 851 of the piston position 711.

Figure 9A:
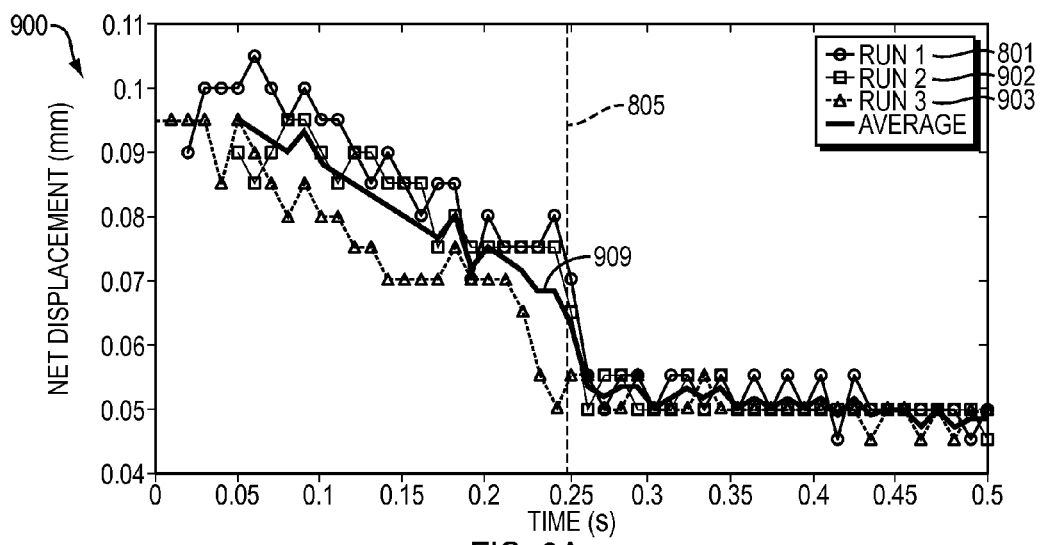
FIGS. 9A-F are the respective graphs of FIGS. 8A-F and two additional data sets generated with the force profile of FIG. 7A including an average of the displacements and the detected removal of a volume of air in the syringe in accordance with aspect of the disclosed embodiment.
Figure 9B:
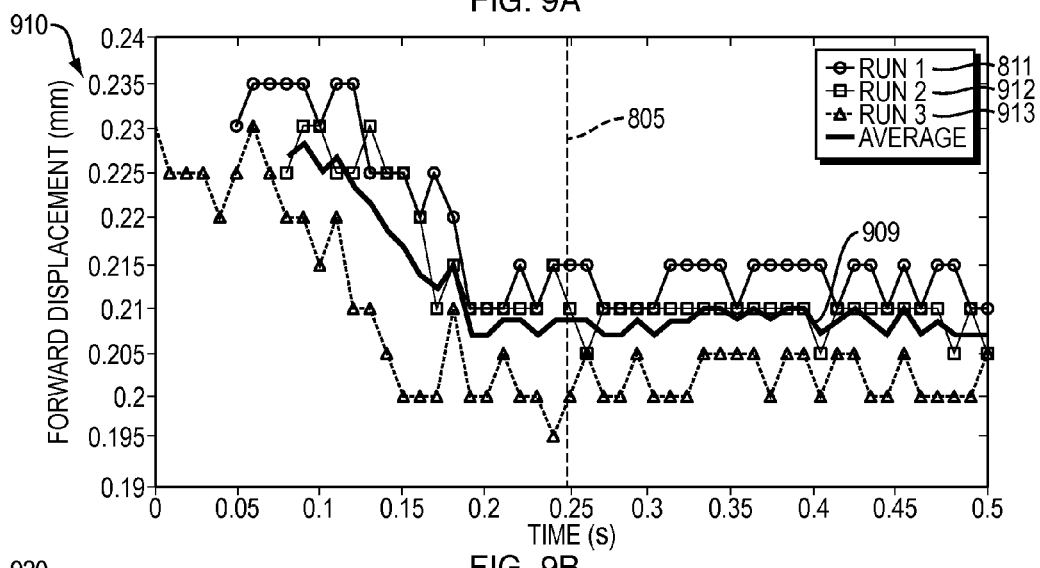
Figure 9C:
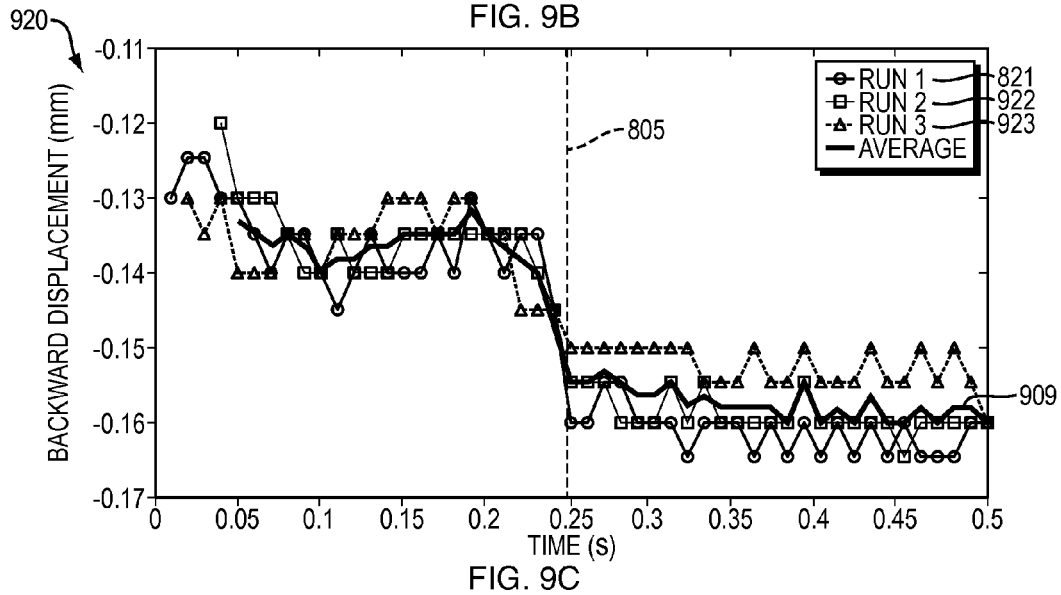
Figure 9D:
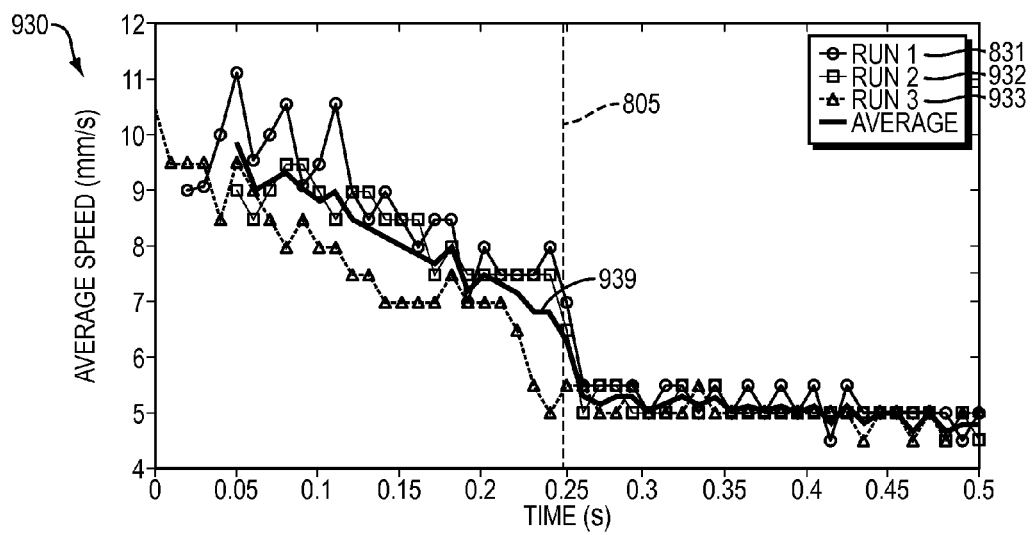
Figure 9E:
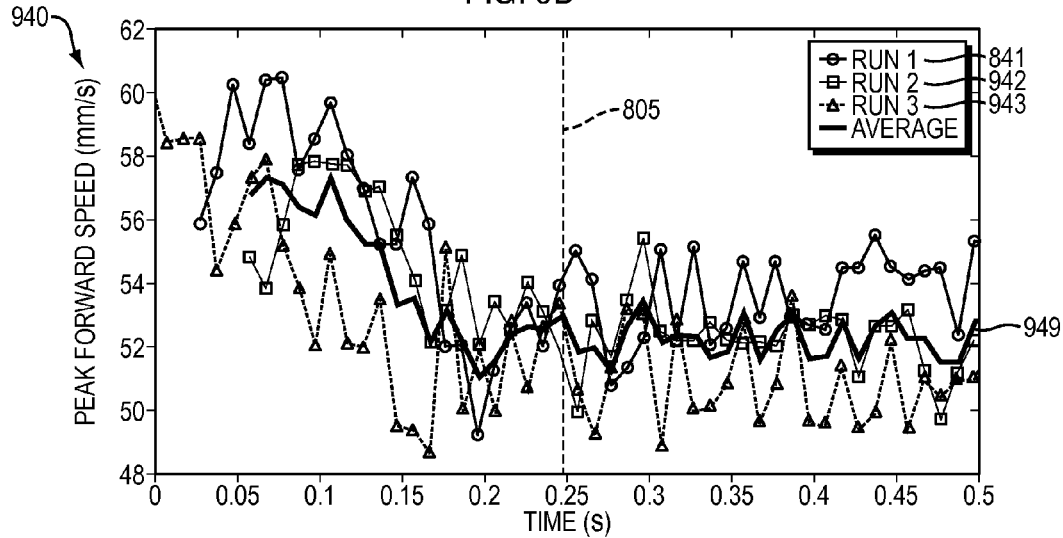
Figure 9F:
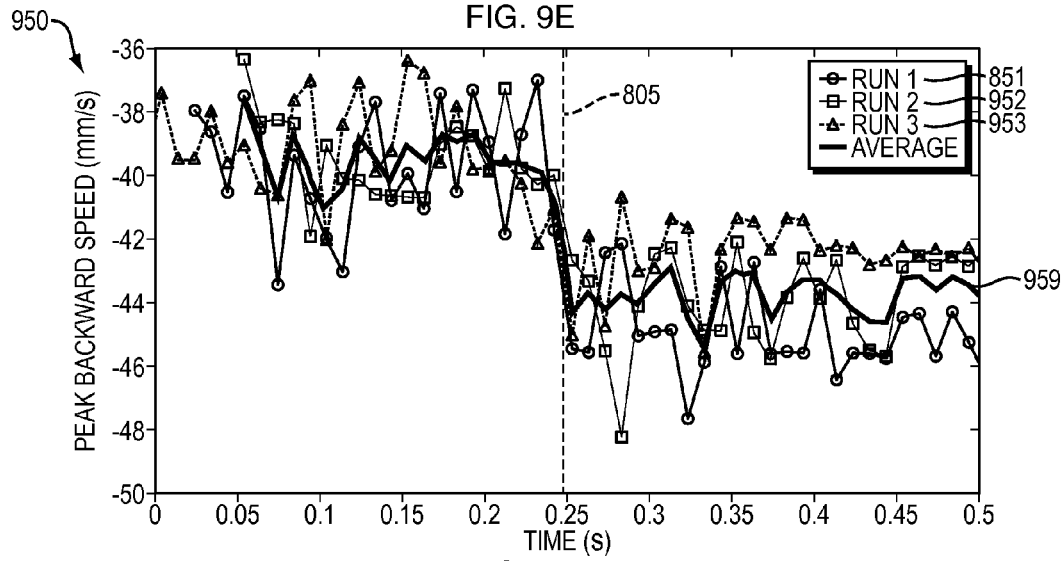
Figure 10A:
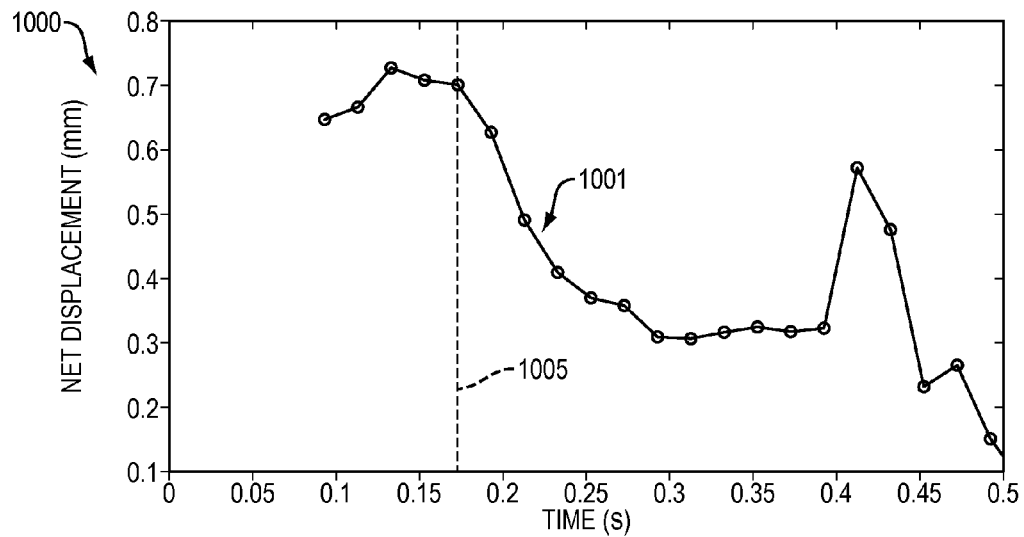
FIGS. 10 A-F are graphs of the net, forward, and backward displacements and net, forward, and backwards speeds, respectively, of a piston driven by 50 Hz oscillating force of the same amplitudes as in FIG. 7A.
Figure 10B:
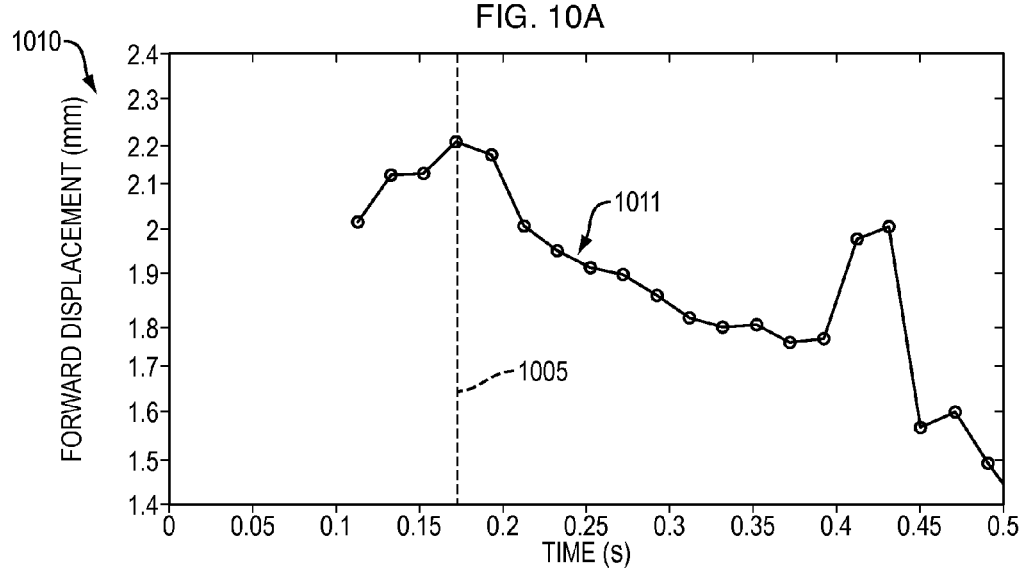
Figure 10C:
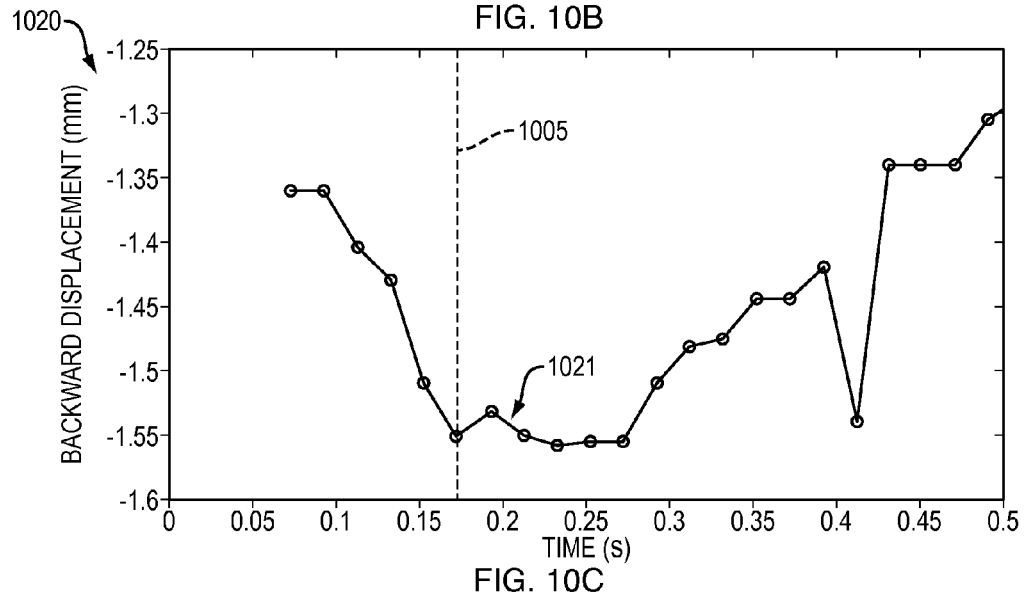
Figure 10D:
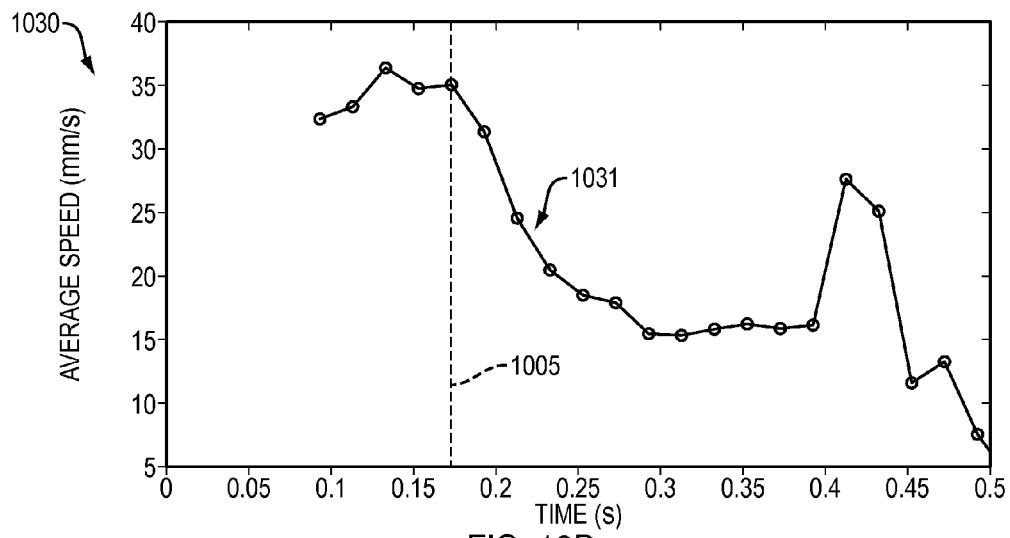
Figure 10E:
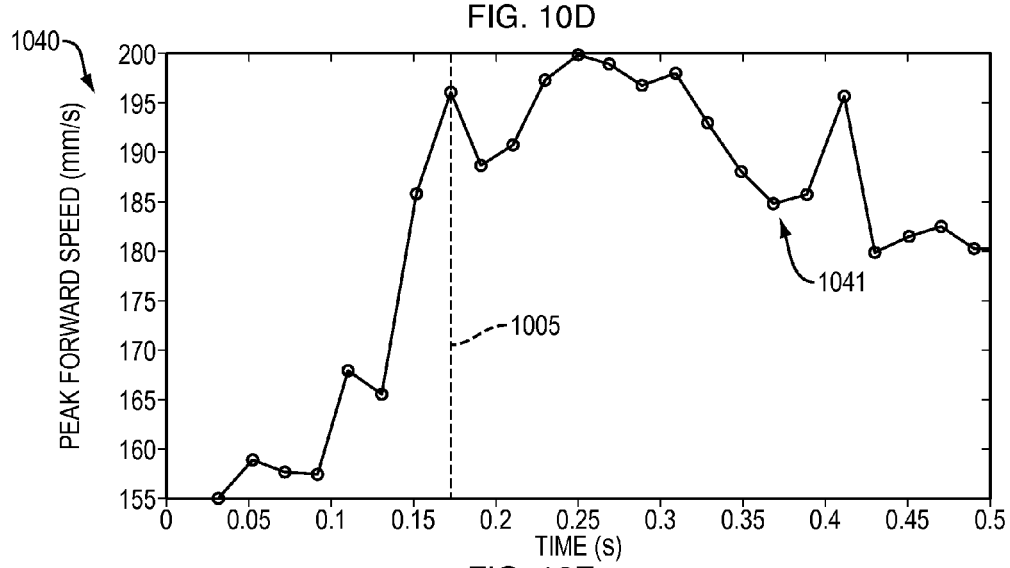
Figure 10F:
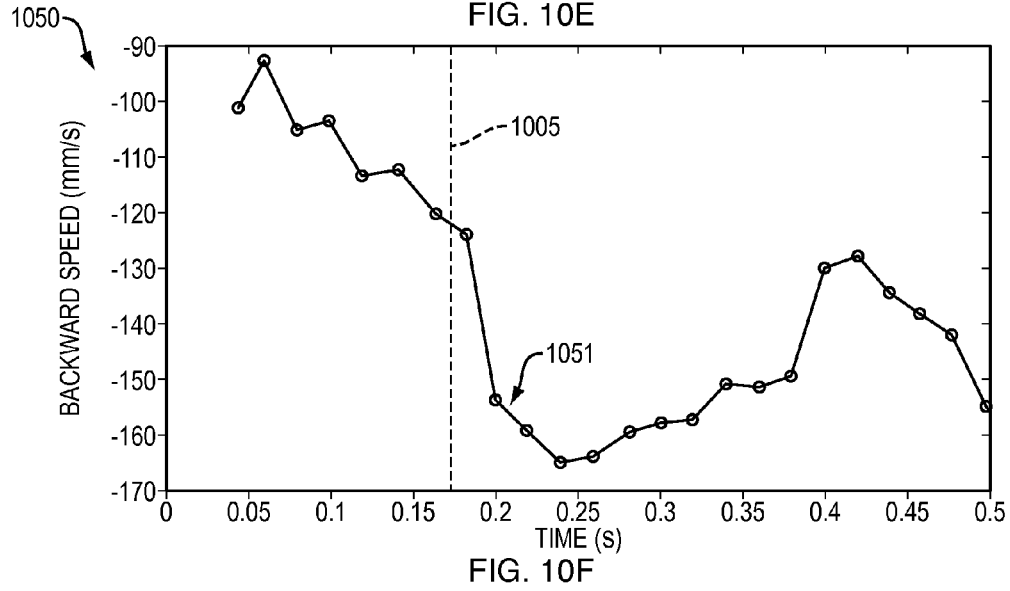

FIGS. 9A-F are the respective graphs of FIGS. 8A-F and two additional data sets generated with the force profile of FIG. 7A applied to different air-to-liquid ratios in accordance with aspect of the disclosed embodiment. FIGS. 9A-F include averages of the displacements and speeds for the three data sets Run 2 and Run 3 have their x-axis shifted to align their bubble detections with the detected bubble removal time 805 of Run 1. FIGS. 9A-C show that the observed trends in displacement per oscillation before and after expulsions of a volume of air 110 for a given mechanical system and fluid agree with the simplified best-fit lines of FIGS. 6A-C. FIGS. 9D-F show that the observed trends in speed before and after expulsions of a volume of air 110 for a given mechanical system display consistencies similar to those shown for displacement in FIGS. 9A-C.

FIGS. 10 A-F are graphs of the net, forward, and backward displacements and net, forward, and backwards speeds, respectively, of a piston driven by 50 Hz oscillating force of the same amplitudes as the FIG. 7A. The detected bubble removal time 1005 is marked and may be based on, for example, a backwards speed threshold of −130 mm/s. FIG. 10A is a displacement vs. time plot 1000 of the net piston displacement 1001. FIG. 10B is a displacement vs. time plot 1010 of the forward piston displacement 1011. FIG. 10C is a displacement vs. time plot 1020 of the backward piston displacement 1021. FIG. 10D is a speed vs. time plot 1030 of the net piston speed 831. FIG. 10E is a speed vs. time plot 1040 of the forward piston speed 1041. FIG. 10F is a speed vs. time plot 1050 of the backward piston speed 1051. FIGS. 10A-D show that even if the higher frequency of FIGS. 8A-F produce easily detectable changes during bubble expulsion events, oscillations at relatively lower frequencies still product detectable position changes during bubble expulsions.

Figure 11A:
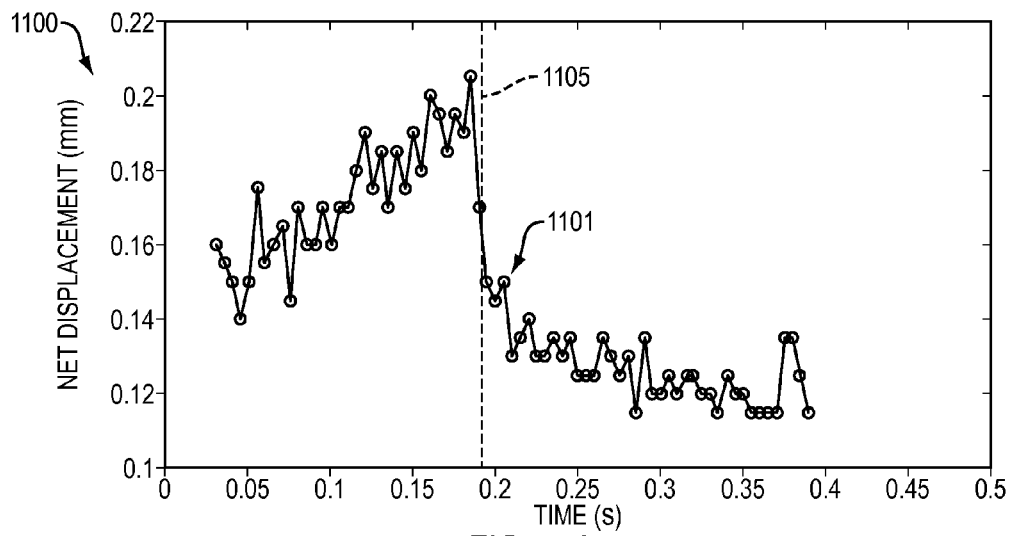
FIGS. 11A-F are graphs of the net, forward, and backward displacements and net, forward, and backwards speeds, respectively, of a piston driven by a 200 Hz oscillating force of the same amplitudes as in FIG. 7A.
Figure 11B:
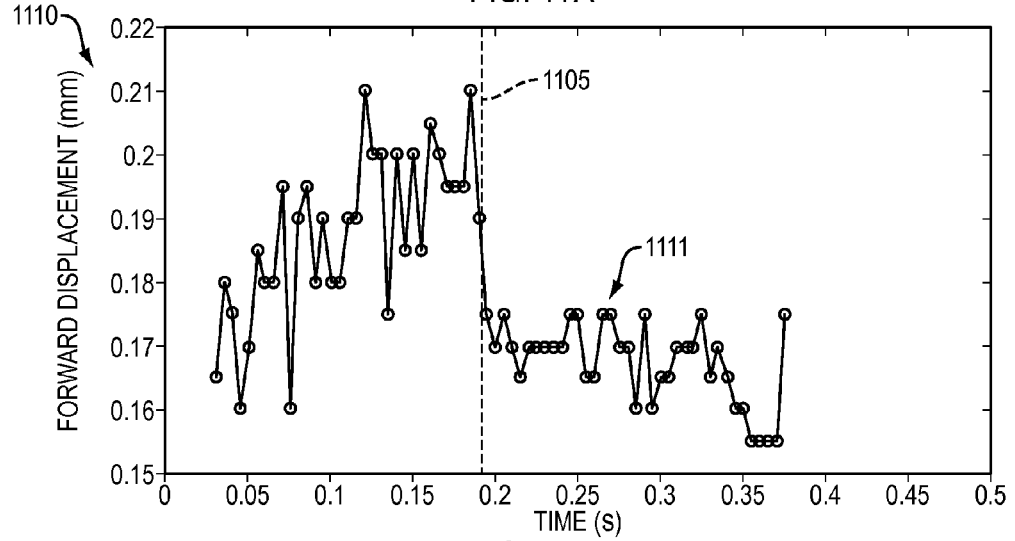
Figure 11C:
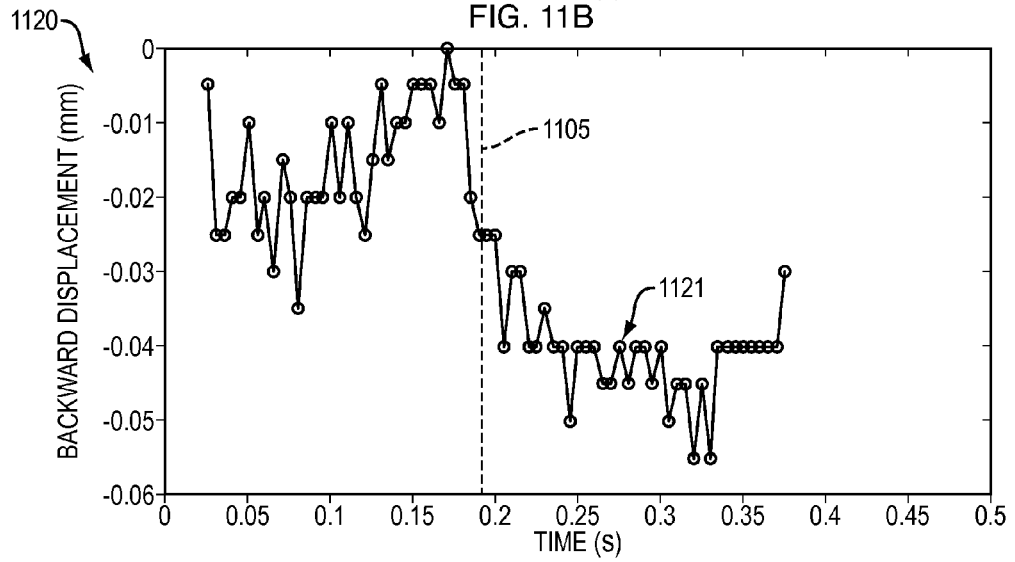
Figure 11D:
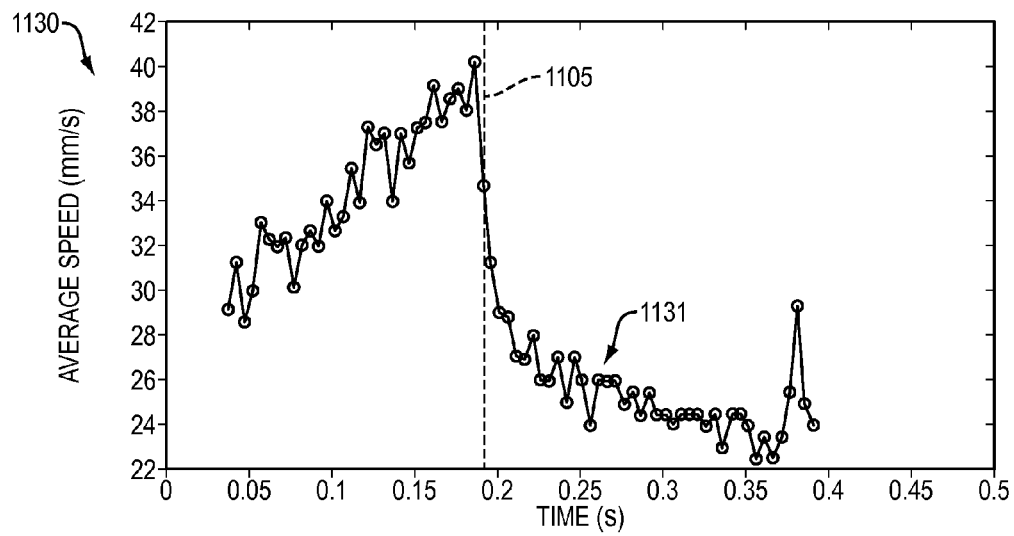
Figure 11E:
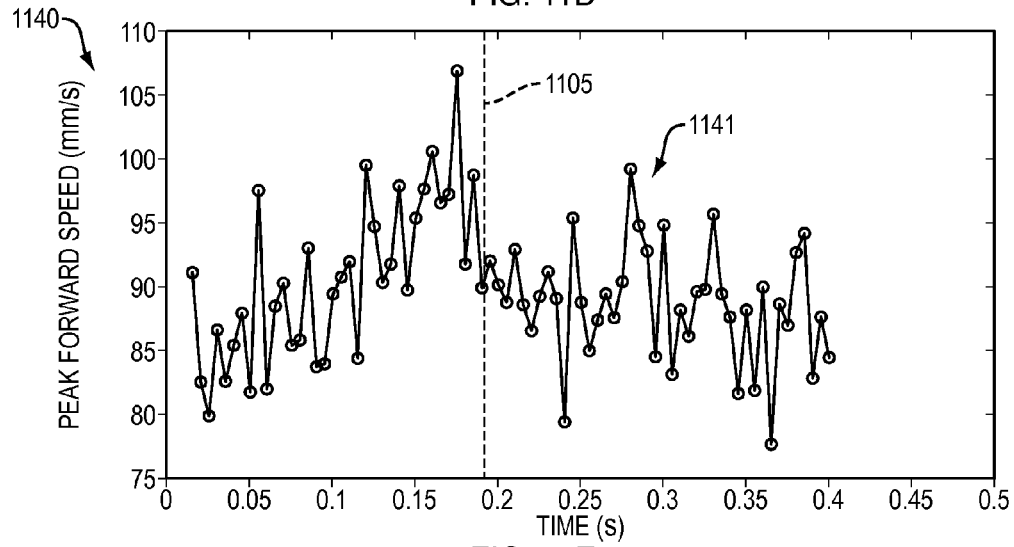
Figure 11F:
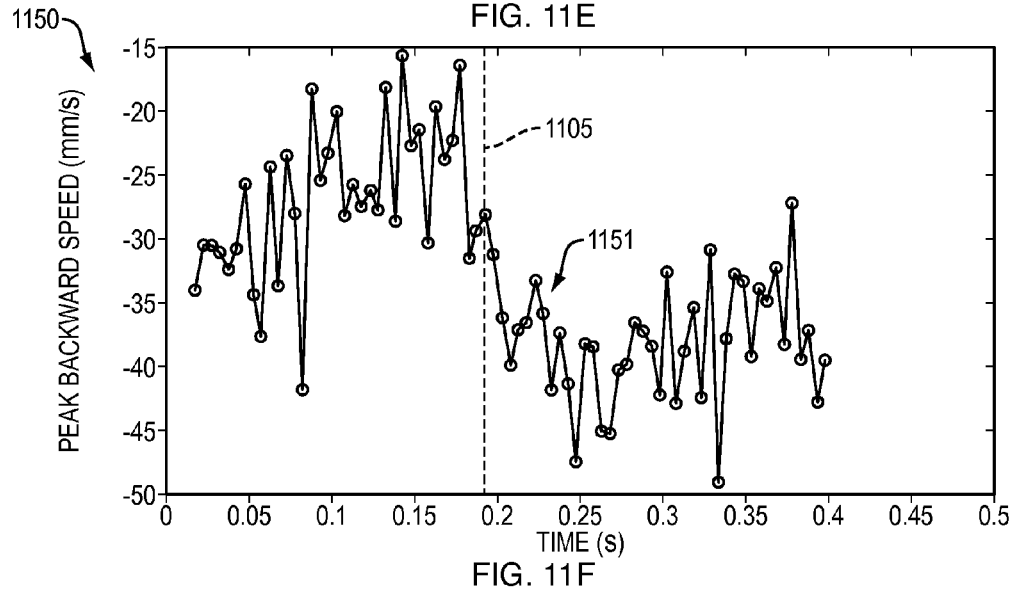

FIGS. 11A-F are graphs of the net, forward, and backward displacements and net, forward, and backwards speeds, respectively, of a piston driven by a 200 Hz oscillating force of the same amplitudes as the FIG. 7A. The detected bubble removal time 1105 is marked and may be based on, for example, an average net speed threshold of 28 mm/s. FIG. 11A is a displacement vs. time plot 1100 of the net piston displacement 1101. FIG. 11B is a displacement vs. time plot 1100 of the forward piston displacement 1111. FIG. 11C is a displacement vs. time plot 1120 of the backward piston displacement 1121. FIG. 11D is a speed vs. time plot 1130 of the net piston speed 1131. FIG. 11E is a speed vs. time plot 1140 of the forward piston speed 1141. FIG. 11F is a speed vs. time plot 850 of the backward piston speed 1151. FIGS. 11A-F show that oscillations at frequencies are close to being attenuated still provide a sufficient signal to detect bubble expulsion. Generally, the 50 Hz data of FIGS. 10A-F and the 200 Hz data of FIGS. 11A-F show that expulsion events that are detectable in position data generated by a wide range of oscillating force frequencies.

Figure 12A:
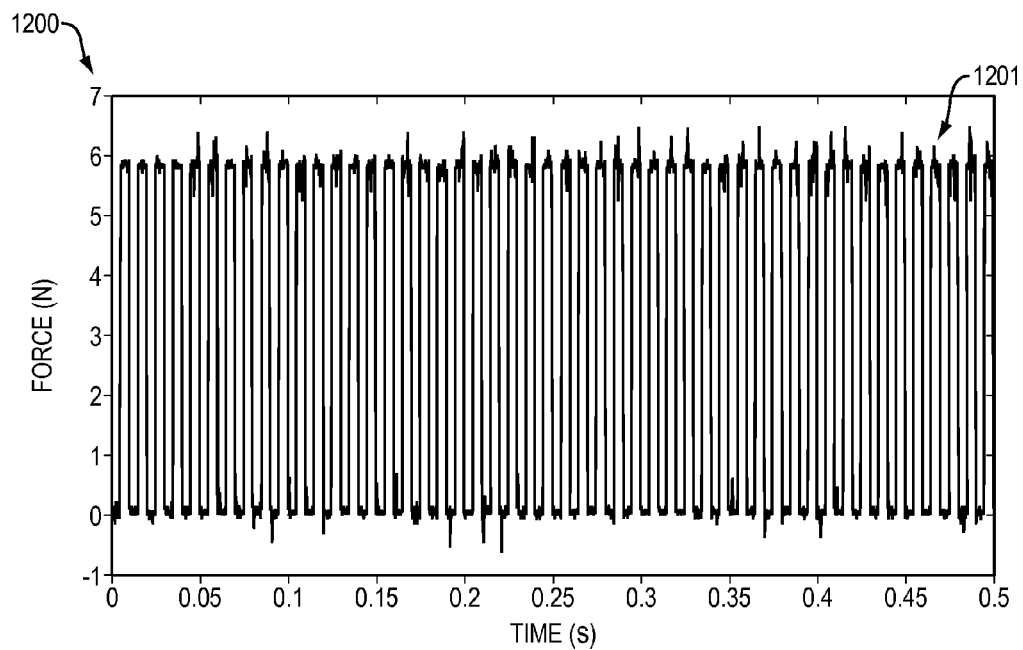
FIGS. 12A-B are graphs of force and position, respectively, of a piston moving in a syringe having a volume of liquid and a volume of air, where the force is oscillating between a positive value and zero, in accordance with aspects of the disclosed embodiment.
Figure 12B:
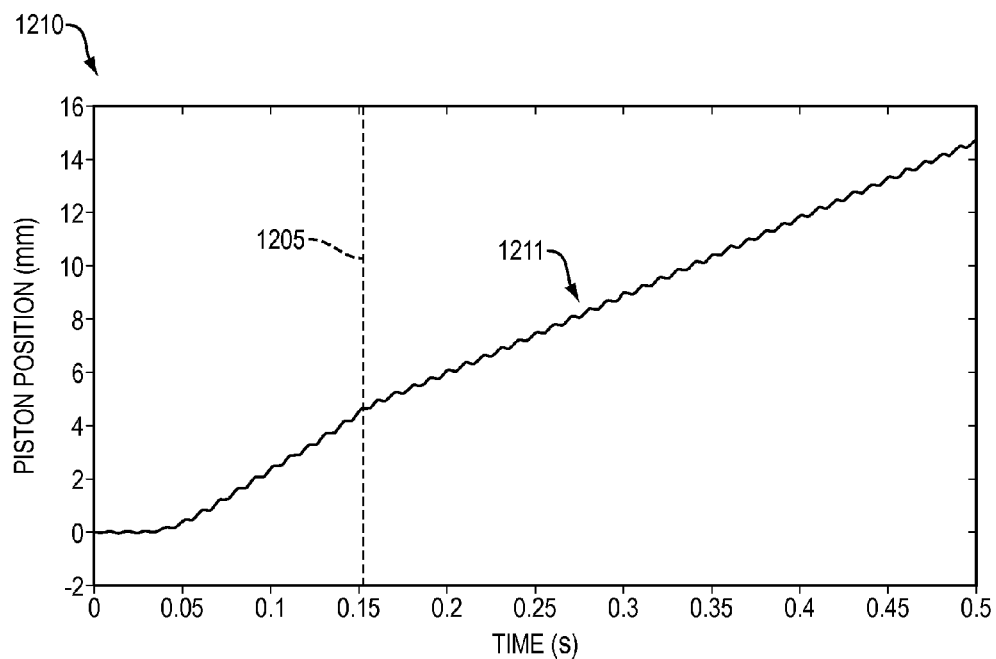

FIGS. 12A-B are graphs of force and position, respectively, of a piston moving in a syringe having a volume of liquid and a volume of air, where the force is oscillating between a positive value and zero, in accordance with aspect of the disclosed embodiment. FIG. 12A is a force vs. time graph 1200 of the force 1201 applied to the pistons of FIG. 12B and FIGS. 13A-F, In FIG. 12A the force 1201 oscillates at 100 Hz between a positive and zero value, 6.0 and 0.0 N respectively. FIG. 12B is a position vs. time graph 1210 of piston position 1211 of a piston 101 in an ampoule 109 having a volume of air 120 and a volume of liquid 110 and a force 211 applied according to FIG. 12B. An inflection point 1205 in the piston position 1211 can be observed around time 0.15 seconds, which reflects an observed fully expelled volume of air from the ampoule 109.

Figure 13A:
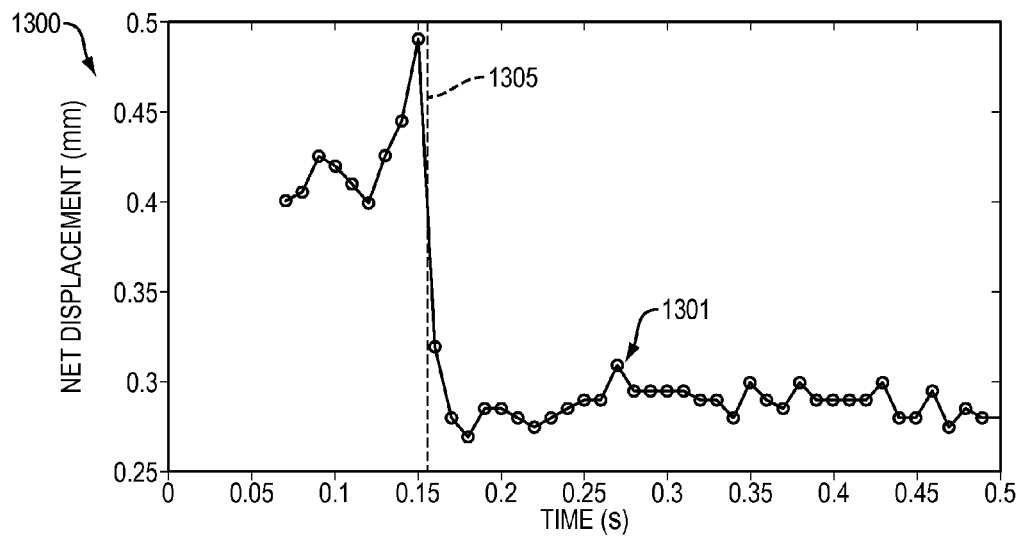
FIGS. 13A-F are graphs of the net, forward, and backward displacements and net, forward, and backwards speeds, respectively, of the piston position of FIG. 12B showing a detectable removal of the volume of air in accordance with aspects of the disclosed embodiment.
Figure 13B:
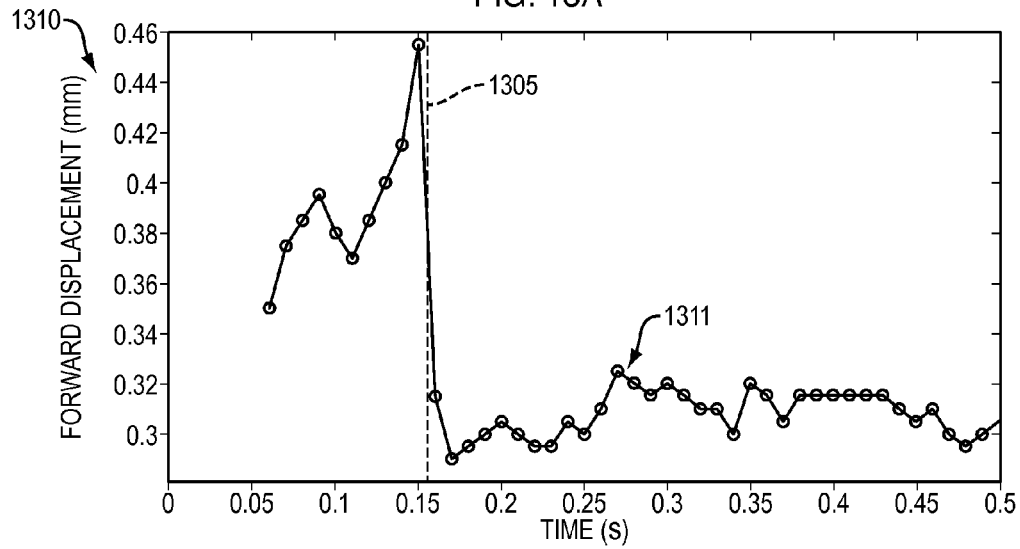
Figure 13C:
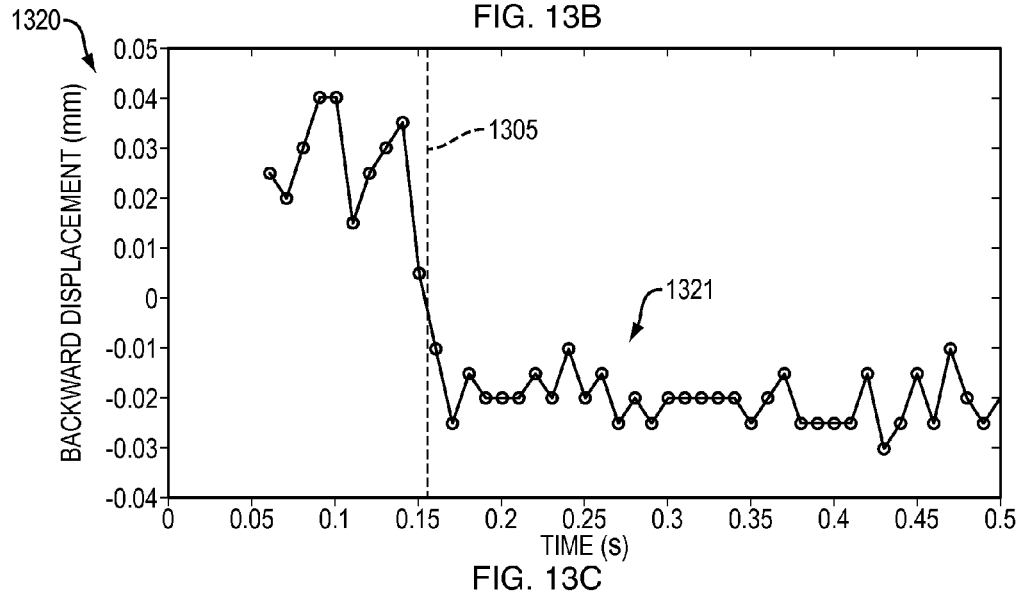
Figure 13D:
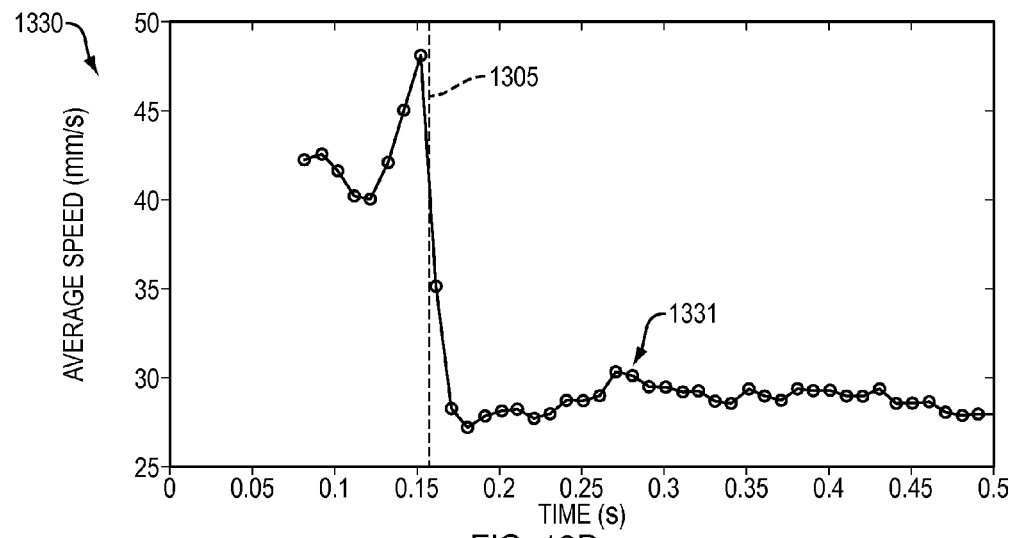
Figure 13E:
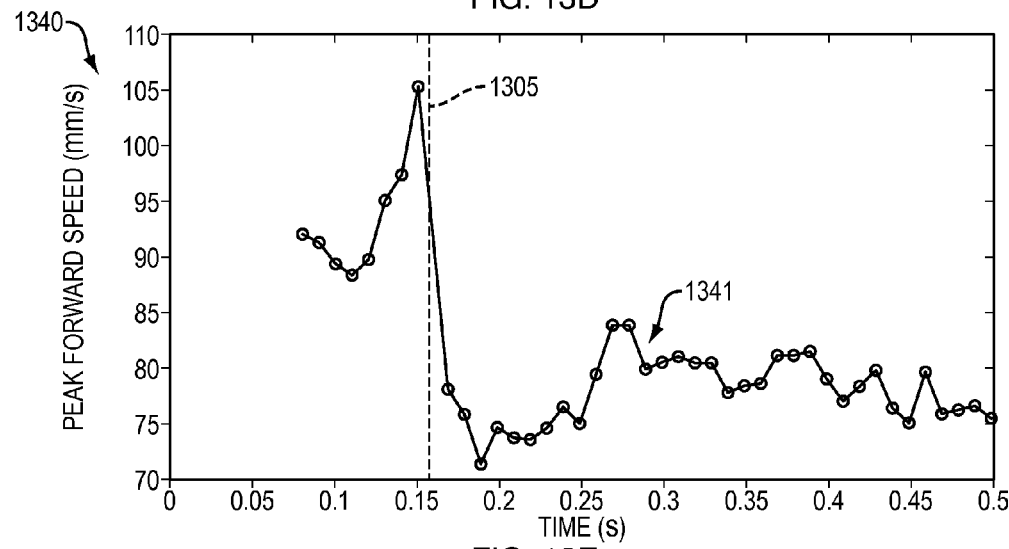
Figure 13F:
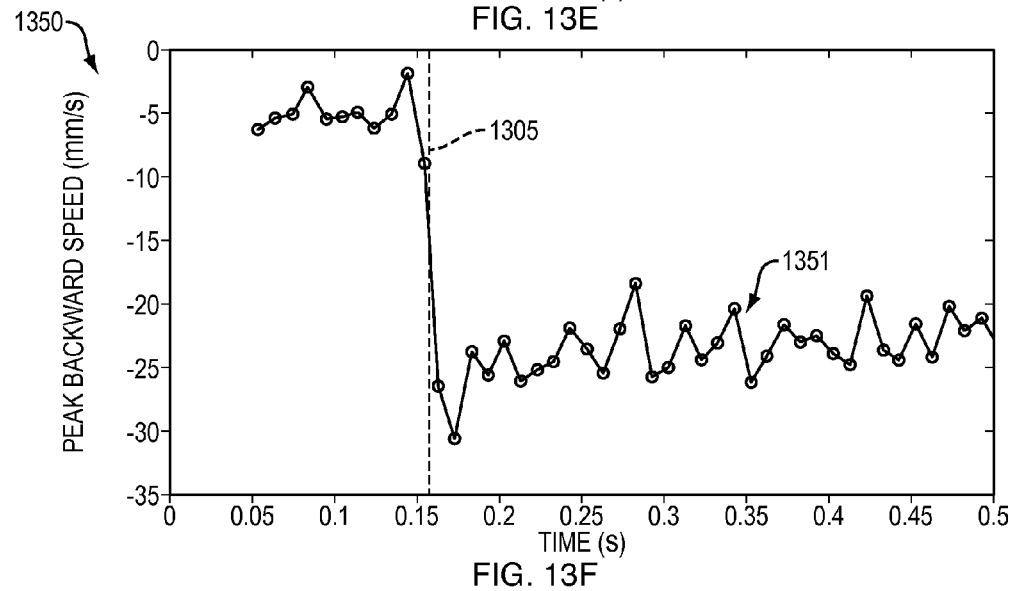

FIGS. 13A-F are graphs of the net, forward, and backward displacements and net, forward, and backwards speeds, respectively, of the piston position of FIG. 12B showing a detectable removal of the volume of air in accordance with aspect of the disclosed embodiment. The detected bubble removal time 1305 is marked and may be based on, for example, a backwards displacement threshold of 0.0 mm. FIG. 13A is a displacement vs. time plot 1300 of the net piston displacement 1301 of the piston position 1211. FIG. 13B is a displacement vs. time plot 1310 of the forward piston displacement 1311 of the piston position 1211. FIG. 13C is a displacement vs. time plot 1320 of the backward piston displacement 1321 of the piston position 1211. FIG. 13D is a speed vs. time plot 1330 of the net piston speed 1331 of the piston position 1211. FIG. 13E is a speed vs. time plot 1340 of the forward piston speed 1341 of the piston position 1211. FIG. 13F is a speed vs. time plot 1350 of the backward piston speed 851 of the piston position 1211. The displacement and speed data of FIGS. 13A-F show that the disclosed methods of bubble detection may be used in situations where backward forces cannot be created, i.e., with an actuator 210 that cannot apply force in the backward direction.

Figure 14A:
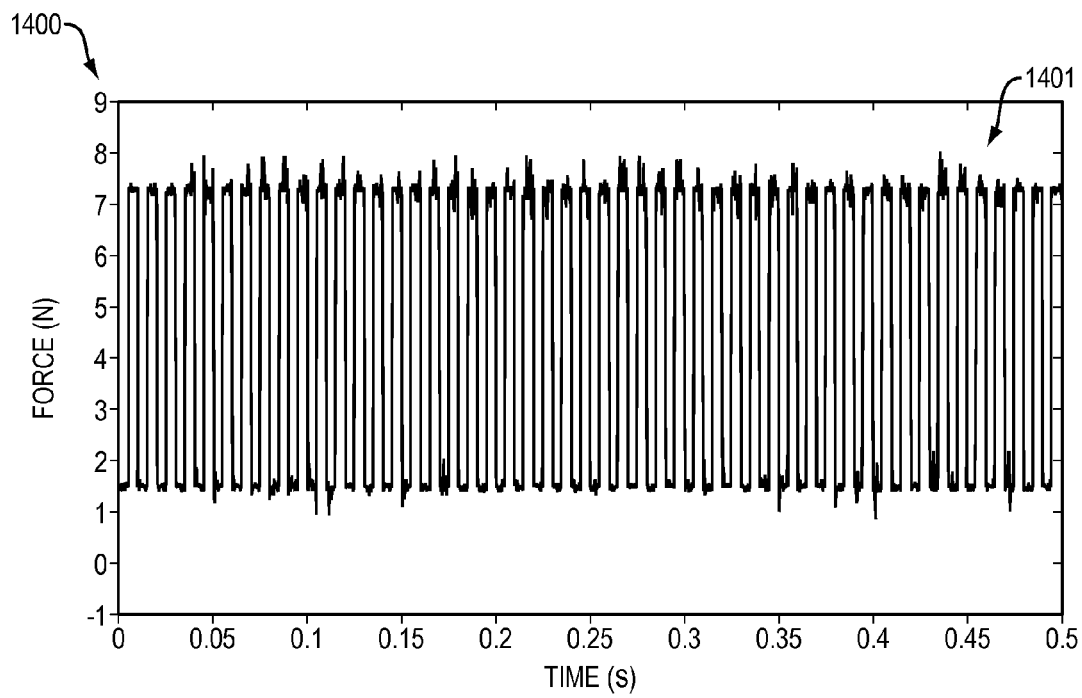
FIGS. 14A-B are graphs of force and position, respectively, of a piston moving in a syringe having a volume of liquid and a volume of air, where the force is oscillating between a positive value and a smaller positive value, in accordance with aspects of the disclosed embodiment.
Figure 14B:
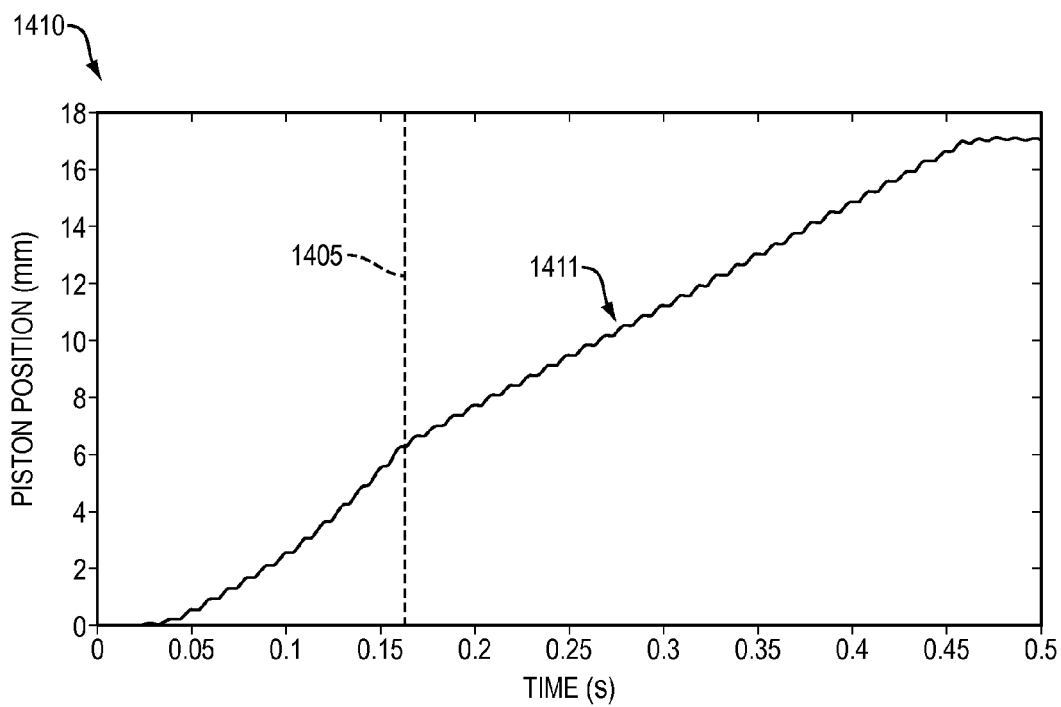

FIGS. 14A-B are graphs of force and position, respectively, of a piston moving in a syringe having a volume of liquid and a volume of air, where the force is oscillating between a positive value and a smaller positive value, in accordance with aspect of the disclosed embodiment. FIG. 14A is a force vs. time graph 1400 of the force 1401 applied to the pistons of FIG. 14B and FIGS. 15A-F. In FIG. 14A the force 1401 oscillates at 100 Hz between a positive and smaller positive value, 7.5 and 2.5 N respectively. FIG. 14B is a position vs. time graph 1410 of piston position 1411 of a piston 101 in an ampoule 109 having a volume of air 120 and a volume of liquid 110 and a force 211 applied according to FIG. 14B. An inflection point 1405 in the piston position 1211 can be observed around time 0.16 seconds, which reflects an observed fully expelled volume of air from the ampoule 109.

Figure 15A:
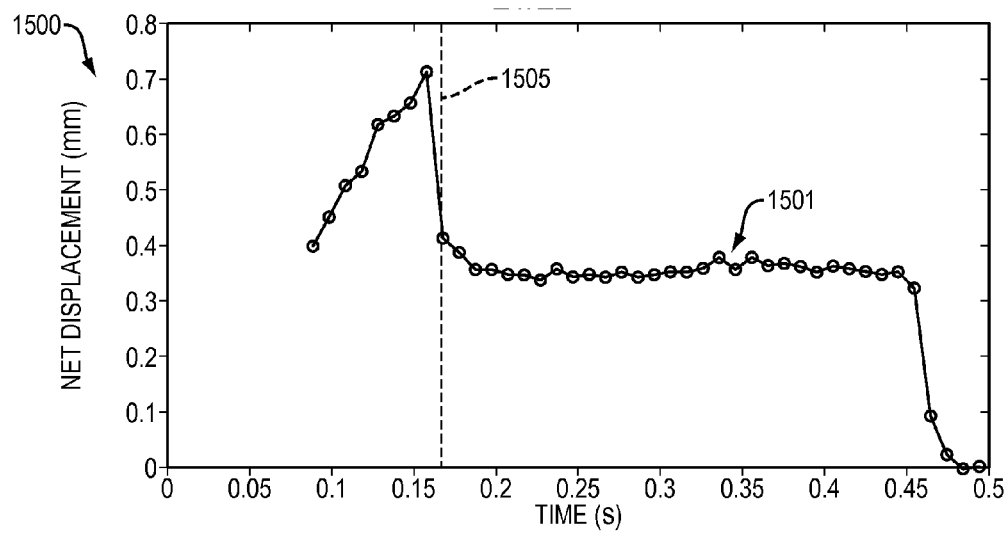
FIGS. 15A-F are graphs of the net, forward, and backward displacements and net, forward, and backwards speeds, respectively, of the piston position of FIG. 14B showing a detectable removal of the volume of air in accordance with aspects of the disclosed embodiment.
Figure 15B:
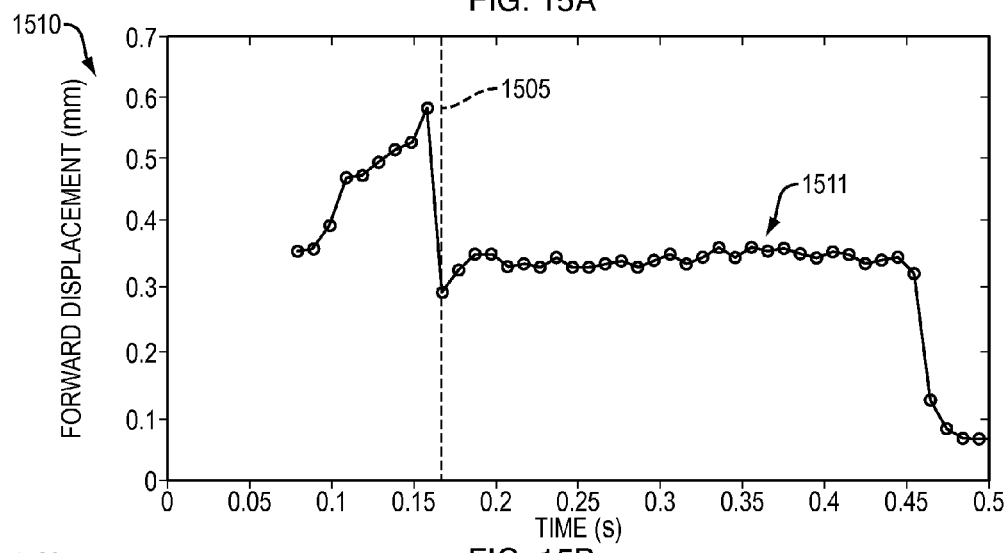
Figure 15C:
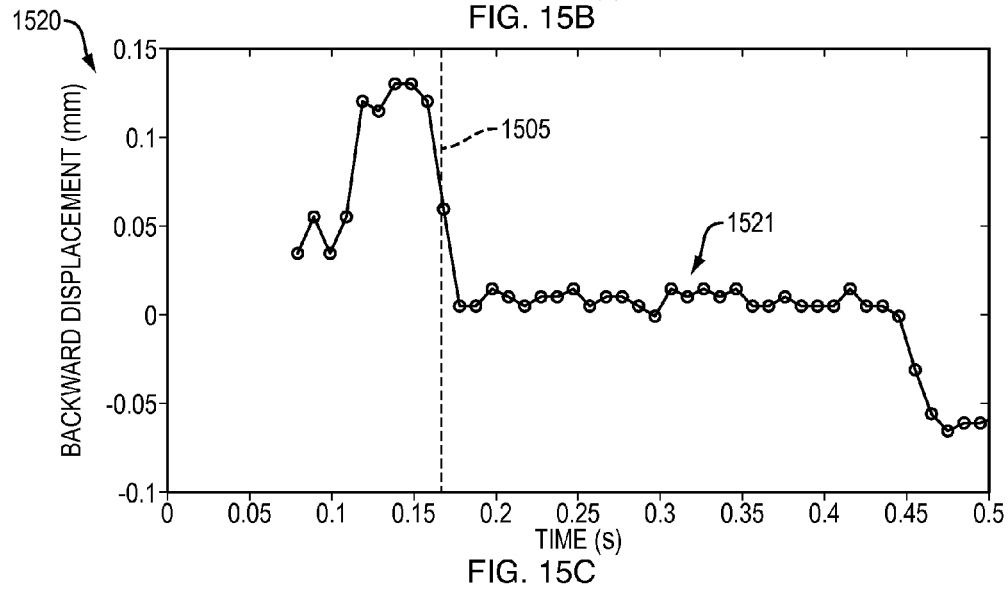
Figure 15D:
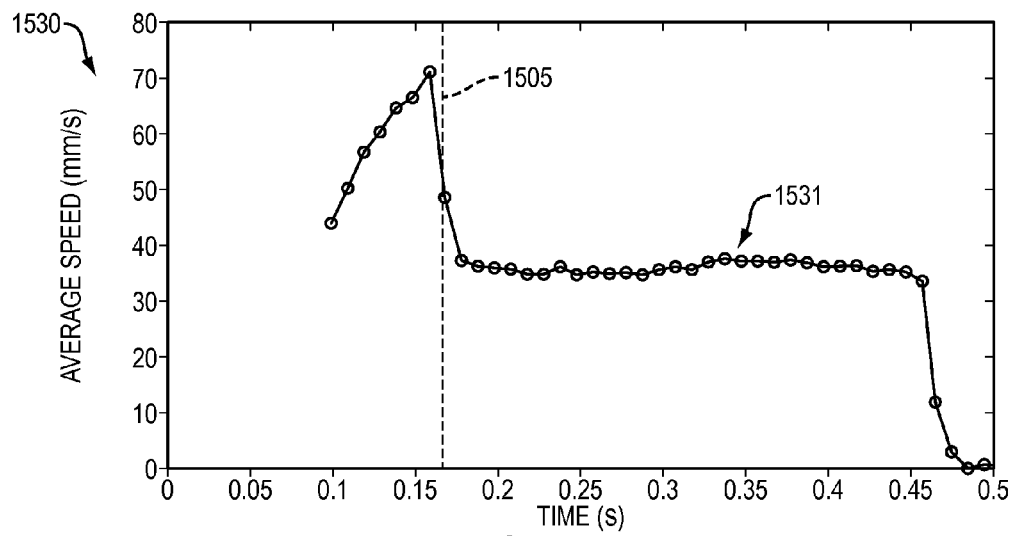
Figure 15E:
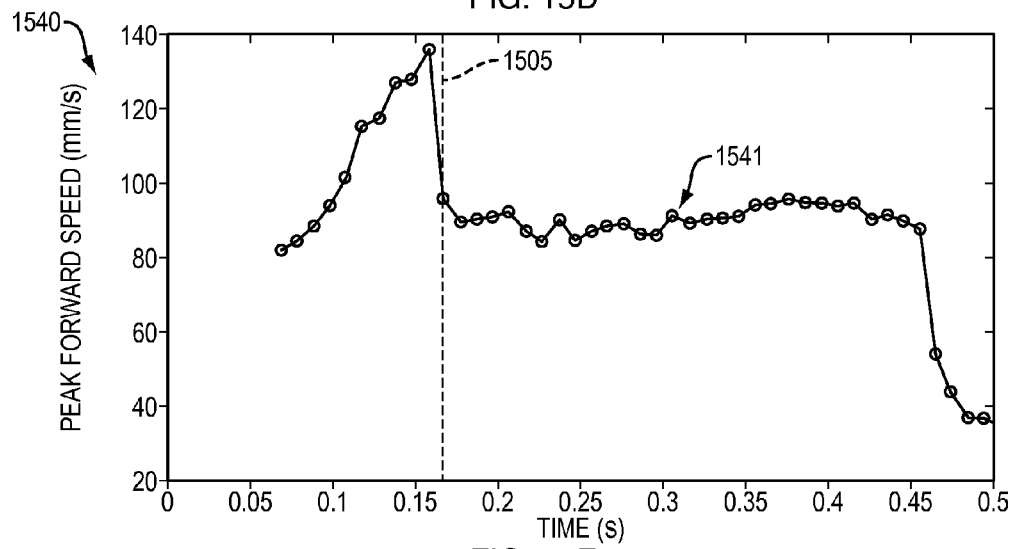
Figure 15F:
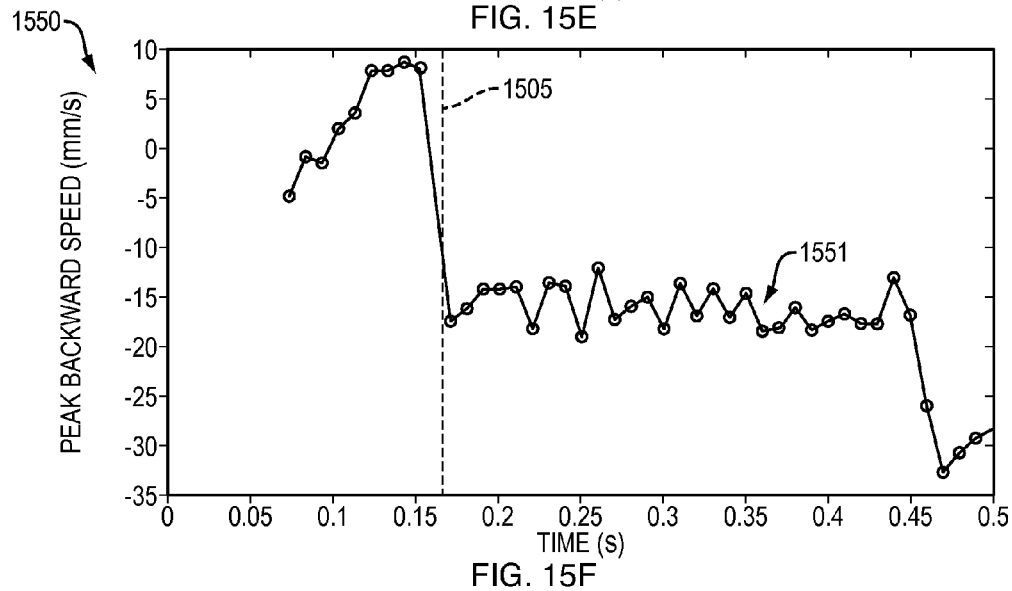

FIGS. 15A-F are graphs of the net, forward, and backward displacements and net, forward, and backwards speeds, respectively, of the piston position of FIG. 14B showing a detectable removal of the volume of air in accordance with aspect of the disclosed embodiment. The detected bubble removal time 1505 is marked and may be based on, for example, a backwards displacement threshold of 0.02 mm. FIG. 15A is a displacement vs. time plot 800 of the net piston displacement 801 of the piston position 1411. FIG. 15B is a displacement vs. time plot 1510 of the forward piston displacement 811 of the piston position 1411. FIG. 15C is a displacement vs. time plot 1520 of the backward piston displacement 1521 of the piston position 1411. FIG. 15D is a speed vs. time plot 1530 of the net piston speed 1531 of the piston position 1411. FIG. 15E is a speed vs. time plot 1540 of the forward piston speed 1541 of the piston position 1411. FIG. 15F is a speed vs. time plot 1550 of the backward piston speed 1551 of the piston position 1411. The data of FIGS. 15A-F shows that the disclosed methods to detect bubbles may be used in situations where any backward displacement of the syringe is not possible or not desired, i.e., the expulsion must be as fast as possible, the actuator 210 can only move in one direction during operation, or the process is being done in an environment where outside air cannot be permitted to possibly re-enter the ampoule 109 as a result of any backwards motion of the piston 110 each oscillation.

While this invention has been particularly shown and described with references to example embodiments thereof, it will be understood by those skilled in the art that various changes in form and details may be made therein without departing from the scope of the invention encompassed by the appended claims.

REFERENCES

[1] Hills, et al. "Ultrasonic Air And Fluid Detector." U.S. Pat. No. 7,987,722.

[2] Blaine, et al. "Method And Apparatus For Detecting Air Bubbles." WIPO Pat. No. 2008042721.

[3] Yauchi, et al. "Air-Bubble Detection Apparatus Of Ink Jet Recording Head, And Method And Apparatus For Restoring Ink Jet Recording Head." U.S. Pat. No. 5,500,657.

[4] Bridge, et al. "Bubble Detection System." U.S. Pat. No. 5,059,171.

[5] Kanayama. "Ink Jet Air Bubble Detection." U.S. Pat. No. 4,498,088.

[6] Ciavarini, et al. "Bubble Detection And Recovery In A Liquid Pumping System." U.S. Pat. No. 5,823,747.

What is claimed is:

1. A method of automatically detecting and removing air from a syringe containing a volume of liquid and a volume of gas, the method comprising:

with an actuator controlled by a controller, applying oscillating force to move a piston in the syringe to expel gas through an orifice of the syringe;

sensing a pattern of oscillations of the piston in the syringe and electrically communicating the pattern to the controller;

in the controller, determining when the volume of gas is expelled from the syringe based on a change in the sensed pattern of oscillations; and stopping movement of the piston upon determining that the volume of gas is expelled from the orifice.

2. The method of claim 1, wherein applying the oscillating force to the piston further includes applying at least one of the following in alternation to the piston: a positive and a negative force, a positive and a zero force, and a first positive force and a second positive force, and wherein determining when the volume of gas is expelled from the syringe is based on a change in the sensed pattern of oscillations of the piston during one or more oscillation or based on a comparison to a given reference value.

3. The method of claim 1, wherein sensing the pattern of oscillations of the piston includes sensing a displacement of the piston, and wherein determining when the volume of gas is expelled from the syringe is based on a change in the sensed displacement of the piston.

4. The method of claim 3, wherein sensing the displacement of the piston includes sensing a forward displacement of the piston for each oscillation, and wherein determining when the volume of gas is expelled from the syringe is based on the sensed forward displacement of the piston.

5. The method of claim 3, wherein sensing the displacement of the piston includes sensing a backwards displacement of the piston for each oscillation, and wherein determining when the volume of gas is expelled from the syringe is based the sensed backwards displacement of the piston.

6. The method of claim 1, wherein sensing the pattern of oscillations of the piston includes sensing a speed of the piston, and wherein determining when the volume of gas is expelled from the syringe is based on a change in the sensed speed of the piston.

7. The method of claim 6, wherein sensing the speed of the piston includes sensing a forward speed of the piston during each oscillation, and wherein determining when the volume of gas is expelled from the syringe is based on the sensed forward speed of the piston.

8. The method of claim 7, wherein sensing the speed of the piston includes sensing a backwards speed of the piston during each oscillation, and wherein determining when the volume of gas is expelled from the syringe is based on the sensed backwards speed of the piston.

9. The method of claim 1, wherein the volume of liquid further includes a plurality of bubbles, the oscillating force applied by the actuator aggregating at least a portion of the plurality of bubbles into the volume of gas.

10. The method of claim 1, wherein sensing the pattern of oscillations of the piston further includes sensing a forward speed of the piston, and wherein determining when the volume of gas is expelled from the syringe is based a sensed decrease in the forward speed of the piston.

11. The method of claim 1, wherein determining when the volume of gas is expelled from the orifice includes determining that at least a portion of the volume of liquid is expelled through the orifice.

12. The method of claim 1, wherein moving the piston in the syringe further includes controlling a force applied by an electromagnetic actuator to the piston as a function of the sensed pattern of oscillations of the piston.

13. An apparatus for detecting and removing air from a syringe, the apparatus comprising:
said syringe including a piston and an orifice, the syringe having a volume of liquid and a volume of gas disposed in the syringe between the piston and the orifice, the volume of gas being adjacent to the orifice;
a position sensor adapted to sense a pattern of oscillations of the piston in the syringe;
an actuator adapted to apply an oscillating force to move the piston in the syringe; and
a controller responsive to the position sensor, the controller causing the actuator to move the piston and drive gas from the volume of gas through the orifice, the controller determining when the volume of gas is expelled from the syringe as a function of a change in the sensed pattern of oscillations of the piston and stopping movement of the piston upon the determined that the volume of gas is expelled from the orifice.

14. The apparatus of claim 13, wherein the actuator is a bi-directional Lorentz-force electromagnetic actuator.

15. The apparatus of claim 13, wherein the oscillating force applied to the piston by the actuator includes at least one of the following: a positive force and a negative force, a positive and a zero force, and a first positive force and a second positive force, and wherein the controller determines when the volume of gas is expelled as a function of a change in the sensed pattern of oscillations during one or more oscillations of the piston or as function of the sensed pattern of oscillations as compared to a reference value.

16. The apparatus of claim 13, wherein the position sensor is further adapted to sense displacement of the piston, and wherein the controller determining when the volume of gas is expelled from the syringe is a function of the sensed displacement.

17. The apparatus of claim 16, wherein the position sensor is further adapted to sense forward displacement of the piston for each oscillation, and wherein the controller determines when the volume of gas is expelled as a function of the sensed forward displacement.

18. The apparatus of claim 16, wherein the position sensor is further adapted to sense backwards displacement of the piston for each oscillation, and wherein the controller determines when the volume of gas is expelled as a function of the sensed backwards displacement.

19. The apparatus of claim 13, wherein the position sensor is further adapted to sense speed of the piston, and wherein the controller determining when the volume of gas is expelled from the syringe is a function of the sensed speed.

20. The apparatus of claim 19, wherein the position sensor is further adapted to sense forward speed of the piston during each oscillation, and wherein the controller determines when the volume of gas is expelled as a function of the sensed forward speed.

21. The apparatus of claim 19, wherein the position sensor is further adapted to sense backwards speed of the piston during each oscillation, and wherein the controller determines when the volume of gas is expelled as a function of the sensed backwards speed.

22. The apparatus of claim 13, wherein the volume of liquid further includes a plurality of bubbles, the oscillating force applied by the actuator aggregates at least a portion of the plurality of bubbles into the volume of gas.

23. The apparatus of claim 13, wherein the position sensor is adapted to sense a forward speed of the piston, and wherein determining when the volume of gas is expelled from the syringe is a function of a decrease in the sensed forward speed of the piston.

24. The apparatus of claim 13, wherein the controller is further configured to stop movement of the piston upon the determination that at least a portion of the volume of liquid is expelled through the orifice.

25. The apparatus of claim 13, wherein the controller is further configured to modulate a force applied by the actuator to move the piston as a function of the movement of the piston.

* * * * *